(12) United States Patent
Woodburn

(10) Patent No.: US 11,000,322 B2
(45) Date of Patent: May 11, 2021

(54) BONE FIXATION SYSTEM

(71) Applicant: DePuy Synthes Products, Inc., Raynham, MA (US)

(72) Inventor: William Woodburn, Mickleton, NJ (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 41 days.

(21) Appl. No.: 16/136,433

(22) Filed: Sep. 20, 2018

(65) Prior Publication Data

US 2020/0093524 A1 Mar. 26, 2020

(51) Int. Cl.
*A61B 17/80* (2006.01)
*A61B 17/00* (2006.01)

(52) U.S. Cl.
CPC ...... *A61B 17/8057* (2013.01); *A61B 17/8071* (2013.01); *A61B 2017/00477* (2013.01)

(58) Field of Classification Search
CPC ...................................... A61B 17/80–17/8095
See application file for complete search history.

(56) References Cited

U.S. PATENT DOCUMENTS

| | | | |
|---|---|---|---|
| 870,242 A | 11/1907 | Meech | |
| 1,182,980 A | 5/1916 | Converse | |
| 2,035,308 A | 3/1936 | Ferber | |
| 3,488,779 A * | 1/1970 | Christensen | .......... A61F 2/3099 623/16.11 |
| 3,805,302 A | 4/1974 | Mathys | |
| 4,429,690 A | 2/1984 | Angelino-Pievani | |
| 5,053,036 A | 10/1991 | Perren et al. | |
| 5,704,936 A | 1/1998 | Mazel | |
| 5,713,900 A | 2/1998 | Benzel et al. | |
| 5,975,904 A | 11/1999 | Spiegel | |
| 6,030,389 A | 2/2000 | Wagner et al. | |
| 6,053,921 A | 4/2000 | Wagner et al. | |
| 6,060,641 A * | 5/2000 | Manolidis | ............. A61F 2/2803 128/898 |
| 6,136,002 A | 10/2000 | Shih et al. | |
| 6,730,091 B1 | 5/2004 | Pfefferle et al. | |
| 6,749,612 B1 | 6/2004 | Conchy et al. | |
| 7,090,676 B2 | 8/2006 | Huebner et al. | |

(Continued)

FOREIGN PATENT DOCUMENTS

| | | |
|---|---|---|
| CN | 1700890 A | 11/2005 |
| CN | 1985770 A | 6/2007 |

(Continued)

*Primary Examiner* — Zade Coley
(74) *Attorney, Agent, or Firm* — BakerHostetler

(57) ABSTRACT

A link for interconnecting with one or more additional, similarly configured links so as to form a linkage for affixation to bone includes a receptacle member having an interior surface that defines a receptacle and further defines a bearing surface and an array of retention features that is arranged around the bearing surface. The link includes an insertion member that extends from the receptacle member and defines an exterior surface that at least partially surrounds a hole. A geometry of the exterior surface is configured to fit within a geometry of the receptacle. The exterior surface defines an annular recess configured to receive a retention member for engaging one or more of the arrayed retention features.

20 Claims, 15 Drawing Sheets

(56) References Cited

U.S. PATENT DOCUMENTS

| | | | |
|---|---|---|---|
| 7,201,753 B2 | 4/2007 | Schlaapfer et al. | |
| 7,935,126 B2 | 5/2011 | Orbay et al. | |
| 7,988,691 B2 | 8/2011 | Schulze et al. | |
| 8,221,472 B2 | 7/2012 | Peterson et al. | |
| 8,343,154 B2 | 1/2013 | Long et al. | |
| 8,343,196 B2 | 1/2013 | Schneider | |
| 8,506,605 B2* | 8/2013 | Bickley | A61B 17/686 606/280 |
| 8,795,277 B2 | 8/2014 | Leuenberger et al. | |
| 9,101,428 B2 | 8/2015 | Long et al. | |
| 10,166,054 B2* | 1/2019 | Woodburn, Sr. | A61B 17/8023 |
| 10,188,439 B2* | 1/2019 | Woodburn | A61B 17/8023 |
| 2001/0034521 A1 | 10/2001 | Bailey et al. | |
| 2002/0183756 A1 | 12/2002 | Michelson | |
| 2004/0039388 A1 | 2/2004 | Biedermann et al. | |
| 2004/0092930 A1 | 5/2004 | Petit et al. | |
| 2004/0102778 A1 | 5/2004 | Huebner et al. | |
| 2004/0116931 A1 | 6/2004 | Carlson | |
| 2005/0027298 A1 | 2/2005 | Michelson | |
| 2005/0154388 A1 | 7/2005 | Roussouly et al. | |
| 2005/0154392 A1 | 7/2005 | Medoff et al. | |
| 2005/0277920 A1 | 12/2005 | Slivka et al. | |
| 2006/0149228 A1 | 7/2006 | Schlapfer et al. | |
| 2007/0123881 A1 | 5/2007 | Ralph et al. | |
| 2007/0233085 A1 | 10/2007 | Biedermann et al. | |
| 2007/0293863 A1 | 12/2007 | Reimels et al. | |
| 2008/0097432 A1 | 4/2008 | Schulze | |
| 2008/0097445 A1 | 4/2008 | Weinstein | |
| 2008/0140130 A1 | 6/2008 | Chan et al. | |
| 2008/0234676 A1 | 9/2008 | Schulze et al. | |
| 2009/0082813 A1* | 3/2009 | Long | A61B 17/80 606/282 |
| 2010/0121328 A1 | 5/2010 | Reitzig et al. | |
| 2010/0179552 A1 | 7/2010 | Wolter | |
| 2010/0274248 A1 | 10/2010 | Overes et al. | |
| 2010/0305569 A1 | 12/2010 | Leuenberger et al. | |
| 2010/0324558 A1* | 12/2010 | Bickley | A61B 17/7059 606/71 |
| 2011/0218534 A1 | 9/2011 | Prandi et al. | |
| 2011/0270316 A1 | 11/2011 | Piehl | |
| 2012/0184995 A1 | 7/2012 | Miller | |
| 2015/0018829 A1* | 1/2015 | Woodburn, Sr. | A61B 17/8047 606/71 |
| 2016/0106485 A1* | 4/2016 | Woodburn | A61B 17/8047 606/71 |
| 2018/0049786 A1 | 2/2018 | Brace et al. | |

FOREIGN PATENT DOCUMENTS

| | | |
|---|---|---|
| CN | 1985771 A | 6/2007 |
| CN | 101594834 A | 12/2009 |
| DE | 202007001585 U1 | 5/2007 |
| EP | 1861030 A2 | 12/2007 |
| JP | 07-501735 | 2/1995 |
| JP | 2002-527137 A | 8/2002 |
| JP | 2007-517584 A | 7/2007 |
| JP | 2009-513245 A | 4/2009 |
| JP | 2010-528706 | 8/2010 |
| WO | 2005/069752 A2 | 8/2005 |
| WO | 2006/102222 A2 | 9/2006 |
| WO | 2007/050276 A2 | 5/2007 |
| WO | 2008/150501 | 12/2008 |
| WO | 2009/049161 A2 | 4/2009 |
| WO | 2015/006188 A1 | 1/2015 |

* cited by examiner

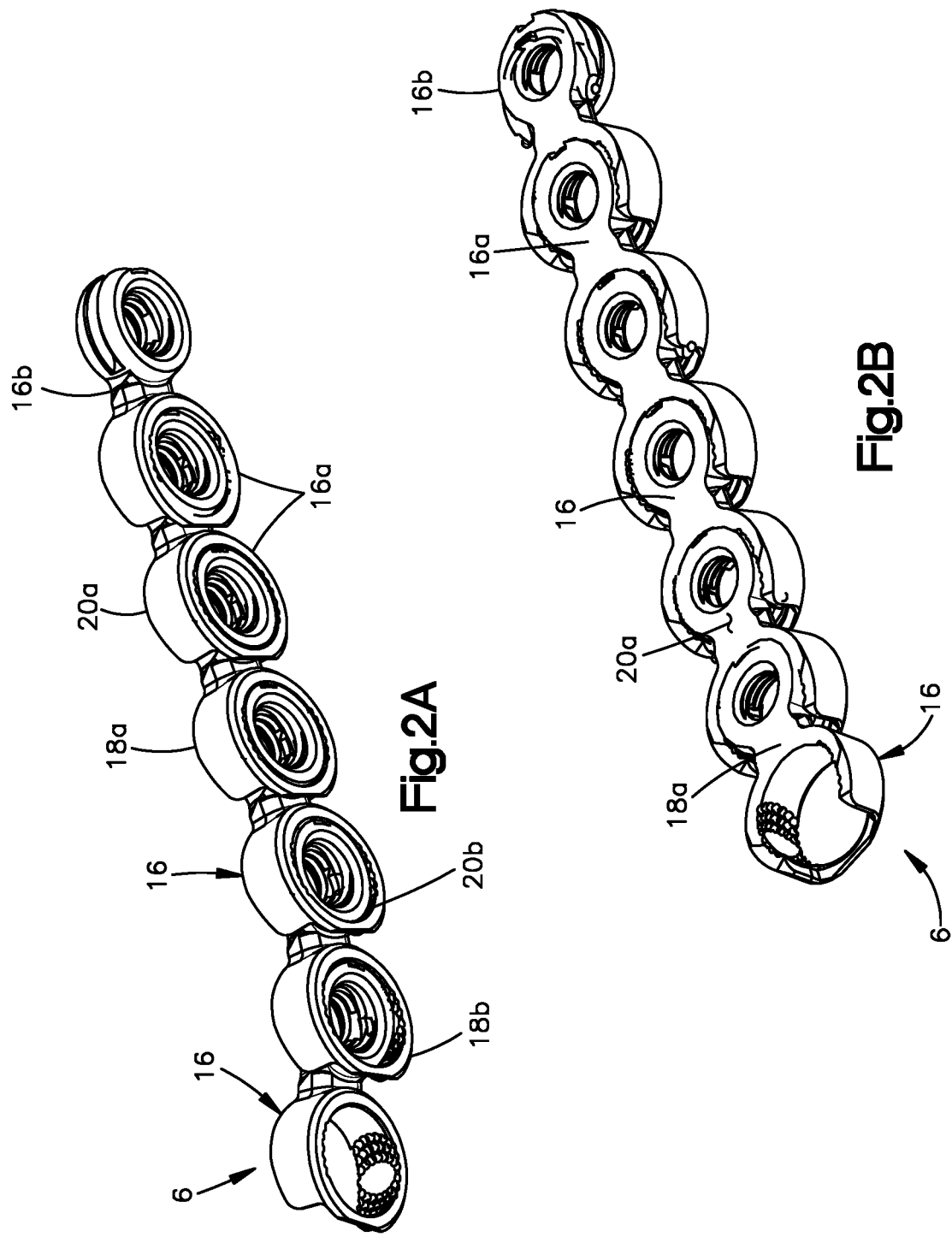

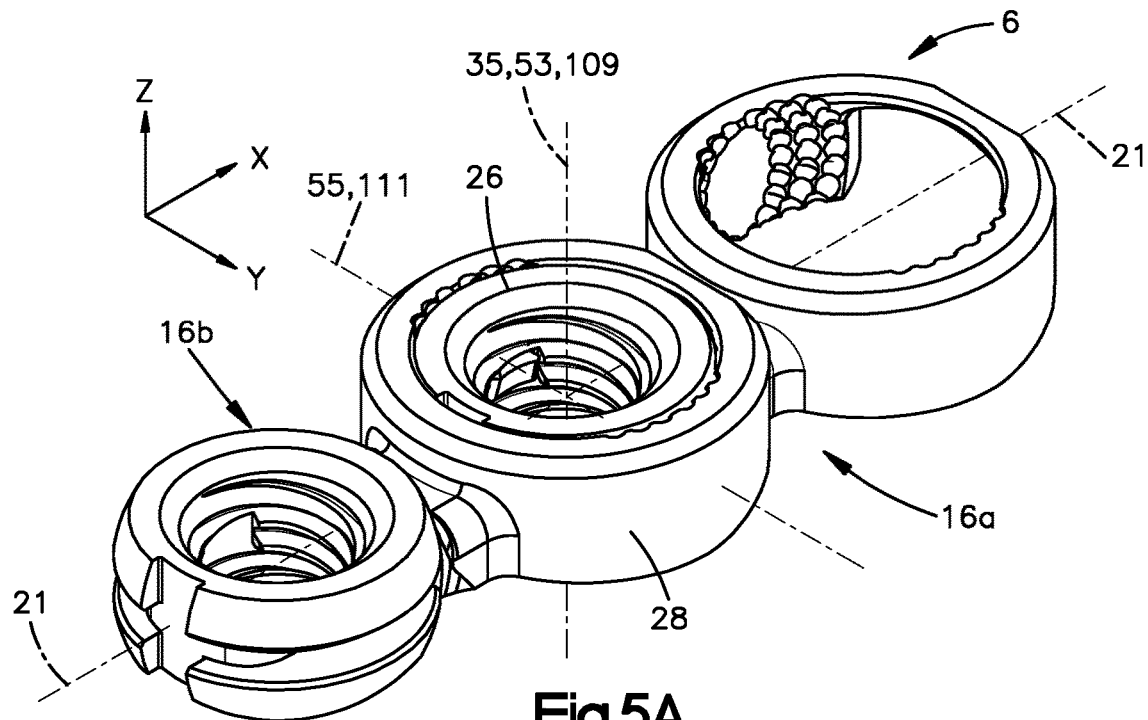
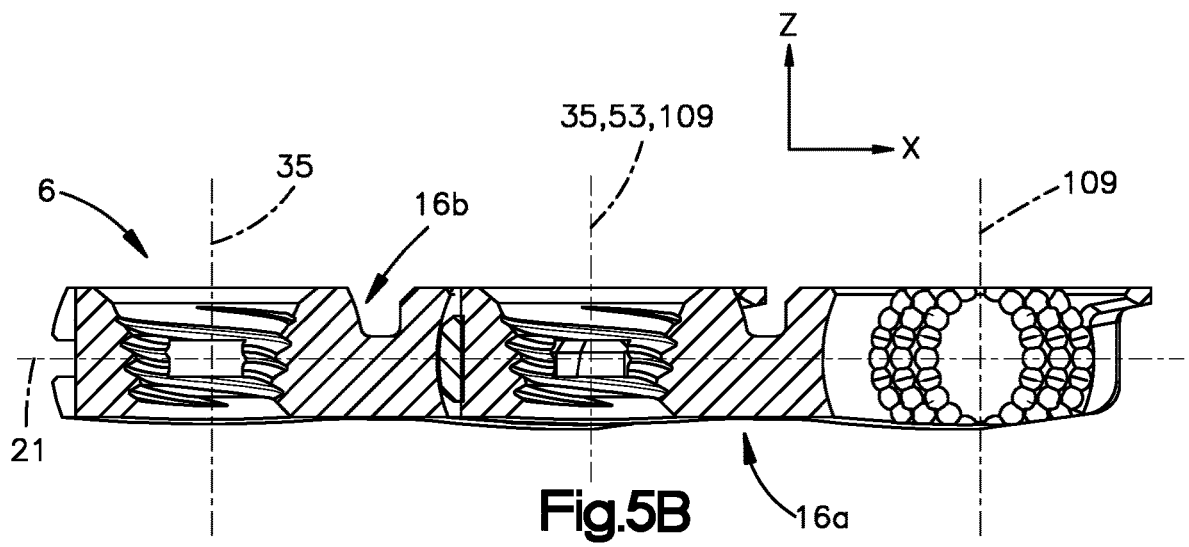
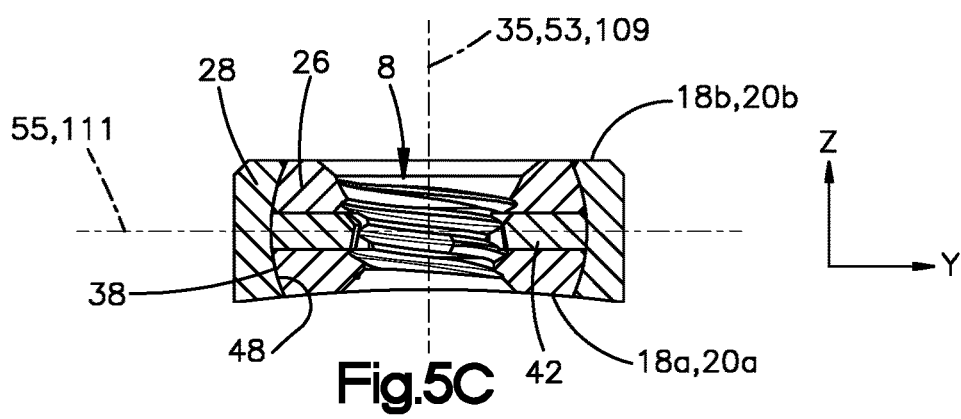

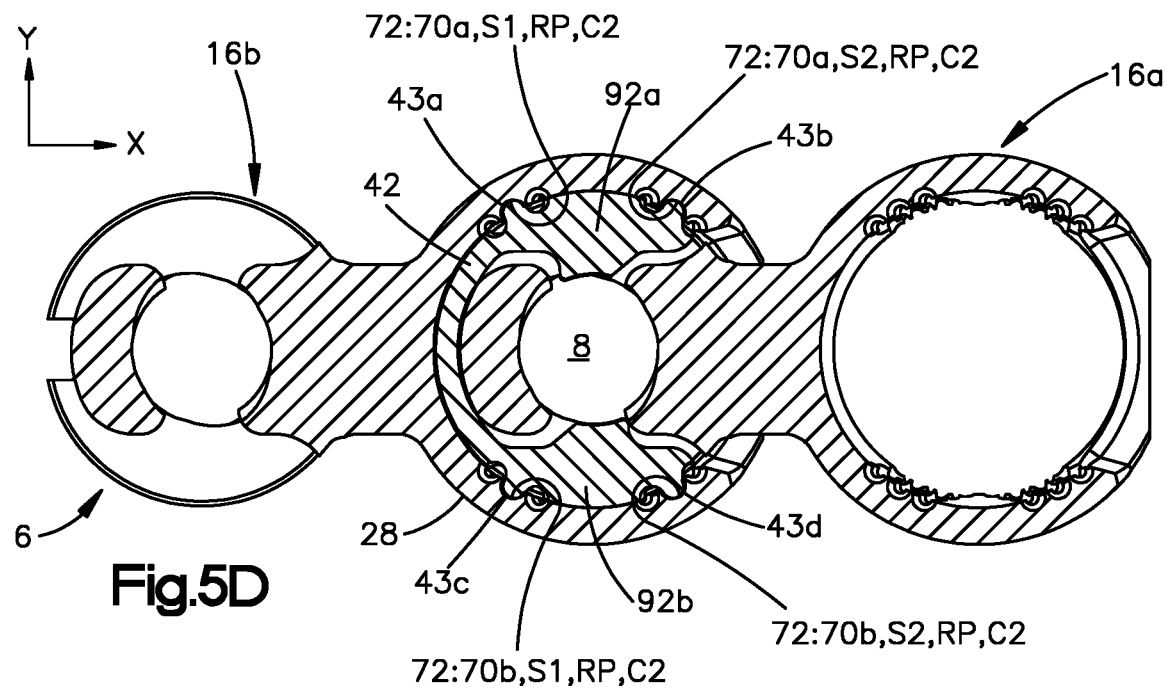
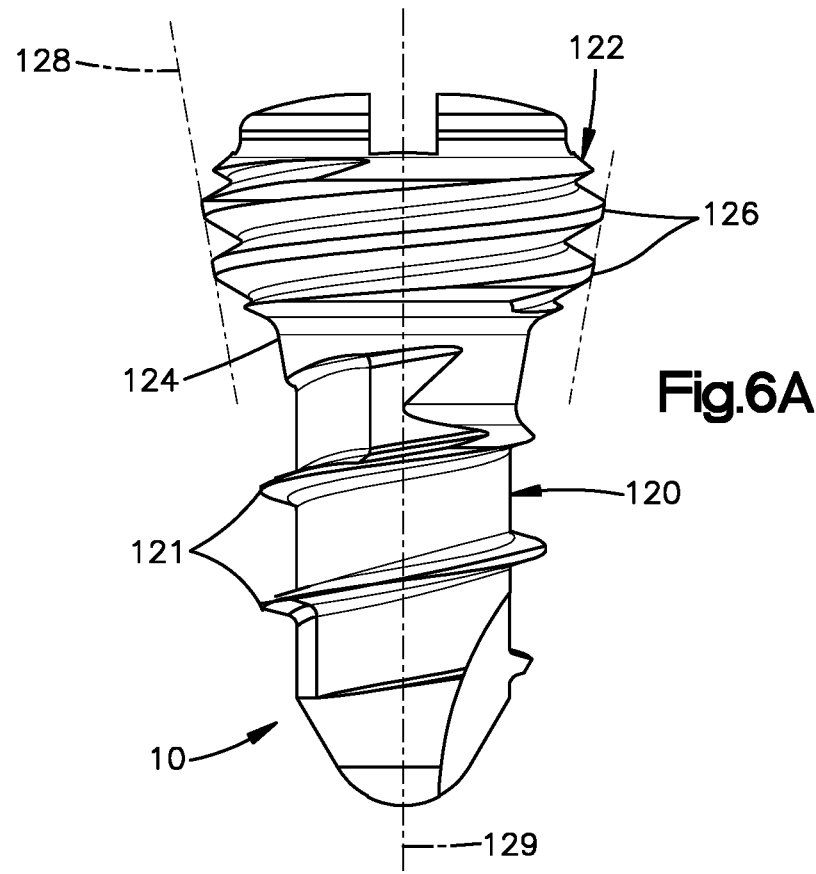

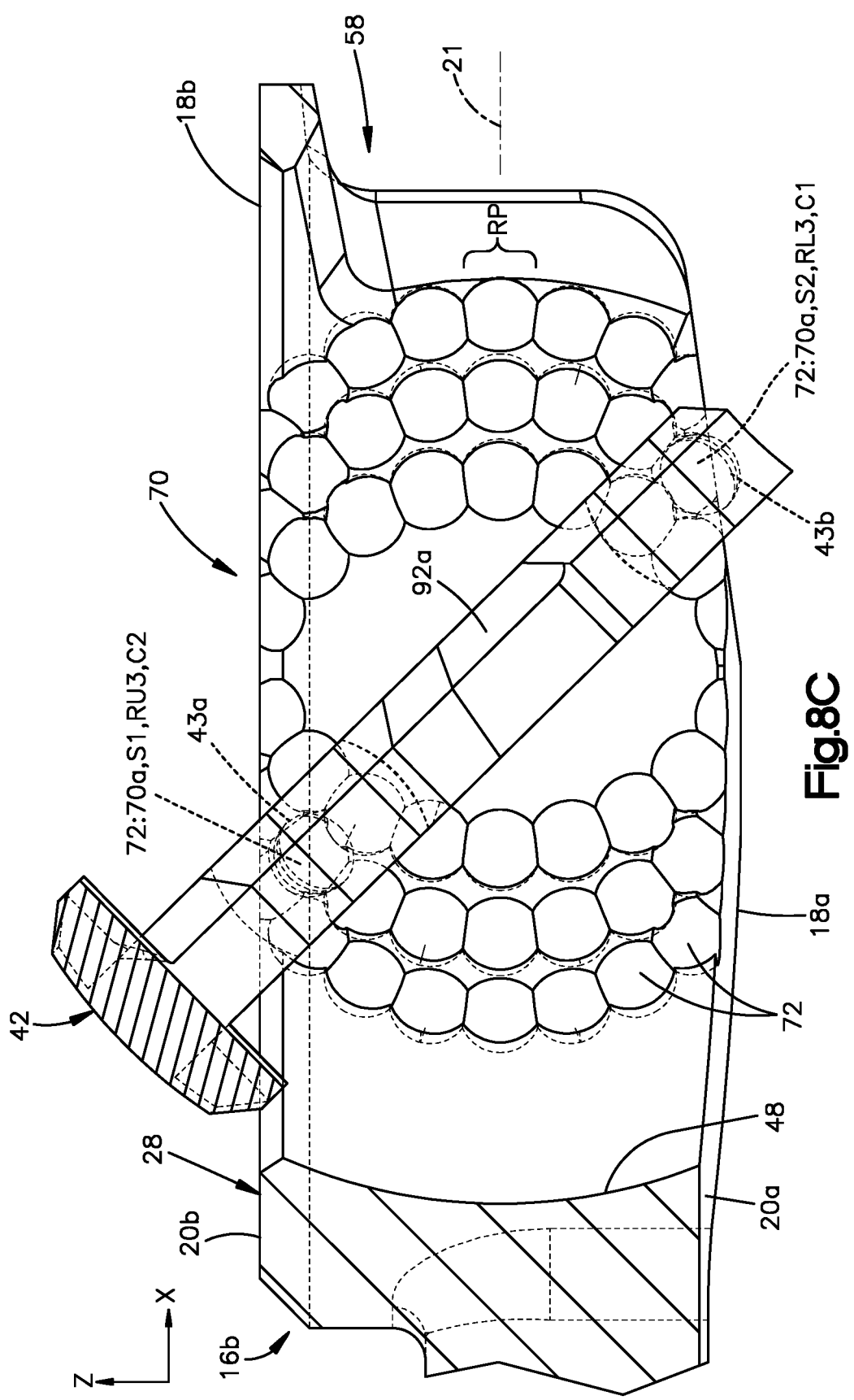

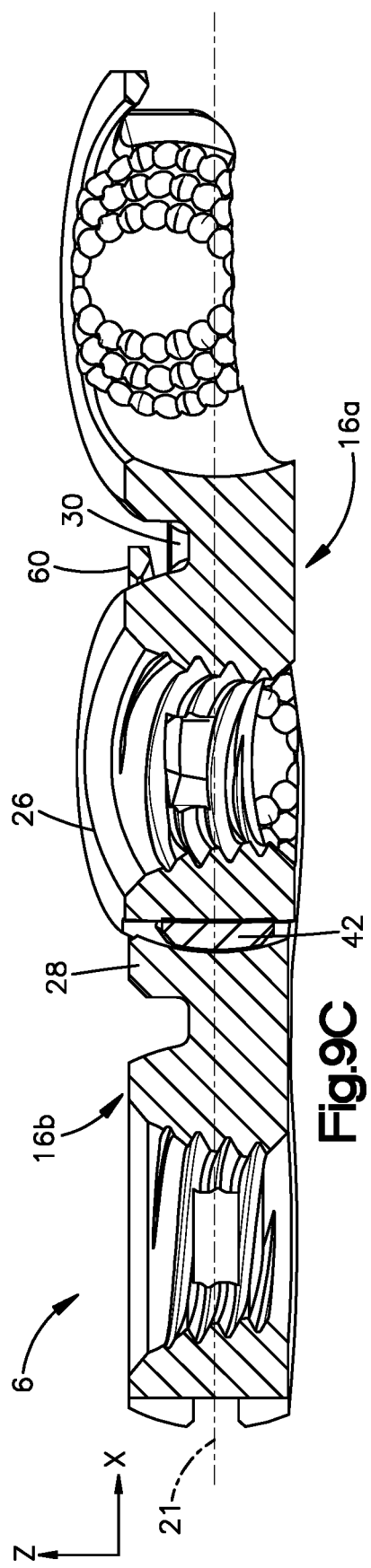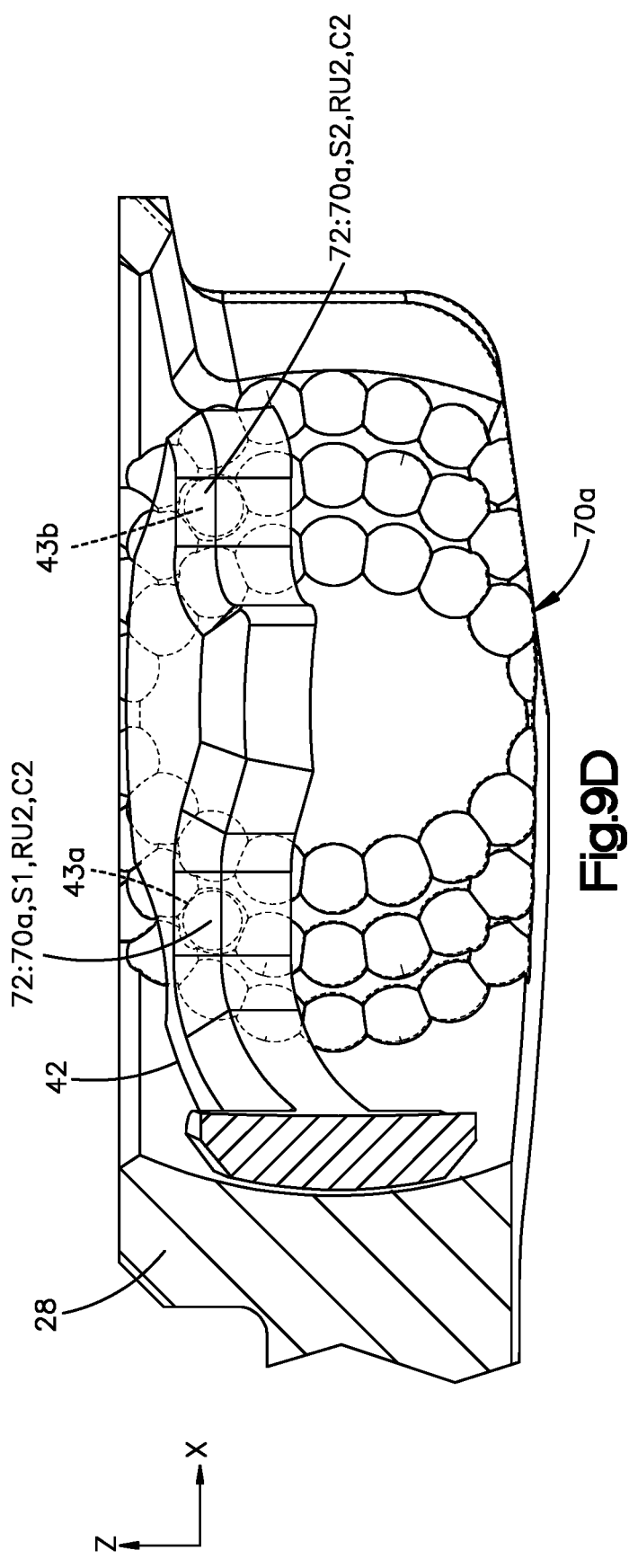

BONE FIXATION SYSTEM

TECHNICAL FIELD

The present disclosure relates generally to bone fixation implants, and in particular relates to an adaptable bone fixation implant that can be readily shaped to repair or replace a particular bone structure of a patient.

BACKGROUND

When bones are damaged through trauma, disease, distraction osteogenesis, or orthognathic surgery, bone fixation implants are commonly used to provide anatomical reduction of bone fragments, to maintain their position, and to ensure union in the desired position. Thus, bone fixation implants are typically designed to achieve proper anatomic fit and function. Additionally, because bone fixation implants often support bones that withstand significant mechanical stress in their anatomic function, such implants are often composed of strong and rigid materials. However, it is particularly difficult to fashion rigid materials to a particular patient's bone contour.

As one example, achieving the proper shape and fit of a bone fixation implant is of particular emphasis in mandibular reconstruction. An improper fit of a mandibular fixation implant may result in disruption of the normal jaw function or alteration of the occlusion, which can cause discomfort for a patient. Additionally, it is desirable for mandibular fixation implants to be strong and rigid to provide a proper occlusion and withstand related mechanical stresses.

SUMMARY

According to an embodiment of the present disclosure, a linkage for affixation to bone includes a first link and a second link that each includes a receptacle member, an insertion member, and a retention member. The receptacle member has an interior surface that defines a receptacle. The interior surface also defines a plurality of retention features. The insertion member extends from the receptacle member and defines an exterior surface that at least partially surrounds a hole and defining a recess. The insertion member also defines at least one opening that extends from the recess to the hole. The exterior surface of the first link is configured to reside within the receptacle of the second link. The retention member of each link is configured to reside within the recess of the link. The retention member defines at least one retention feature configured to engage the plurality of retention features and at least one projection configured to extend internally through the at least one opening and into the hole. The retention member is flexible between a first configuration and a second configuration such that, in the first configuration, the at least one retention feature engages a respective one of the plurality of retention features, and in the second configuration, the at least one retention feature is spaced from the respective one of the plurality of retention features.

According to another embodiment of the present disclosure, a link for interconnecting with one or more additional, similarly configured links so as to form a linkage for affixation to bone includes a receptacle member having an interior surface that defines a receptacle and further defines a bearing surface and an array of retention features that is arranged around the bearing surface. The link includes an insertion member that extends from the receptacle member and defines an exterior surface that at least partially surrounds a hole. A geometry of the exterior surface is configured to fit within a geometry of the receptacle. The exterior surface defines an annular recess configured to receive a retention member for engaging one or more of the arrayed retention features.

BRIEF DESCRIPTION OF THE DRAWINGS

The foregoing summary, as well as the following detailed description of illustrative embodiments of the bone screw of the present application, will be better understood when read in conjunction with the appended drawings. For the purposes of illustrating the bone fixation implant(s) of the present application, there is shown in the drawings illustrative embodiments. It should be understood, however, that the application is not limited to the precise arrangements and instrumentalities shown. In the drawings:

FIG. 2A is an enlarged perspective view of a bone fixation linkage similar to the bone fixation linkage illustrated in FIG. 1, including a plurality of interconnected links;

FIG. 2B is another perspective view of the bone fixation linkage illustrated in FIG. 2A;

FIG. 5A is a perspective view of a linkage including first and second links shown interconnected with each other in a neutral position, wherein the first and second links are each configured as illustrated in FIG. 3B;

FIG. 5B is a sectional side elevation view of the linkage taken along axis 21 of FIG. 5A;

FIG. 5C is a sectional end elevation view of the linkage taken along axis 55 of FIG. 5A;

FIG. 5D is a sectional top plan view of the linkage taken along a plane defined by axes 21 and 55 of FIG. 5A;

FIG. 6A is a side elevation view of a locking member of the linkage, according to an embodiment of the present disclosure;

FIG. 8C is a magnified view of a joint of the linkage illustrated in FIG. 8B, with the first link removed for illustrated purposes;

FIG. 9C is a sectional side elevation view taken along axis 21 illustrated in FIG. 9A; and FIG. 9D is a magnified view of the joint illustrated in FIG. 9C, with the first link removed for illustrated purposes.

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality," as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The embodiments disclosed herein pertain to bone fixation linkages that can be customized quickly to match the shape of the anatomy of a patient, thus reducing the intraoperative "contouring" process, while providing adequate fixation.

Figure 1:
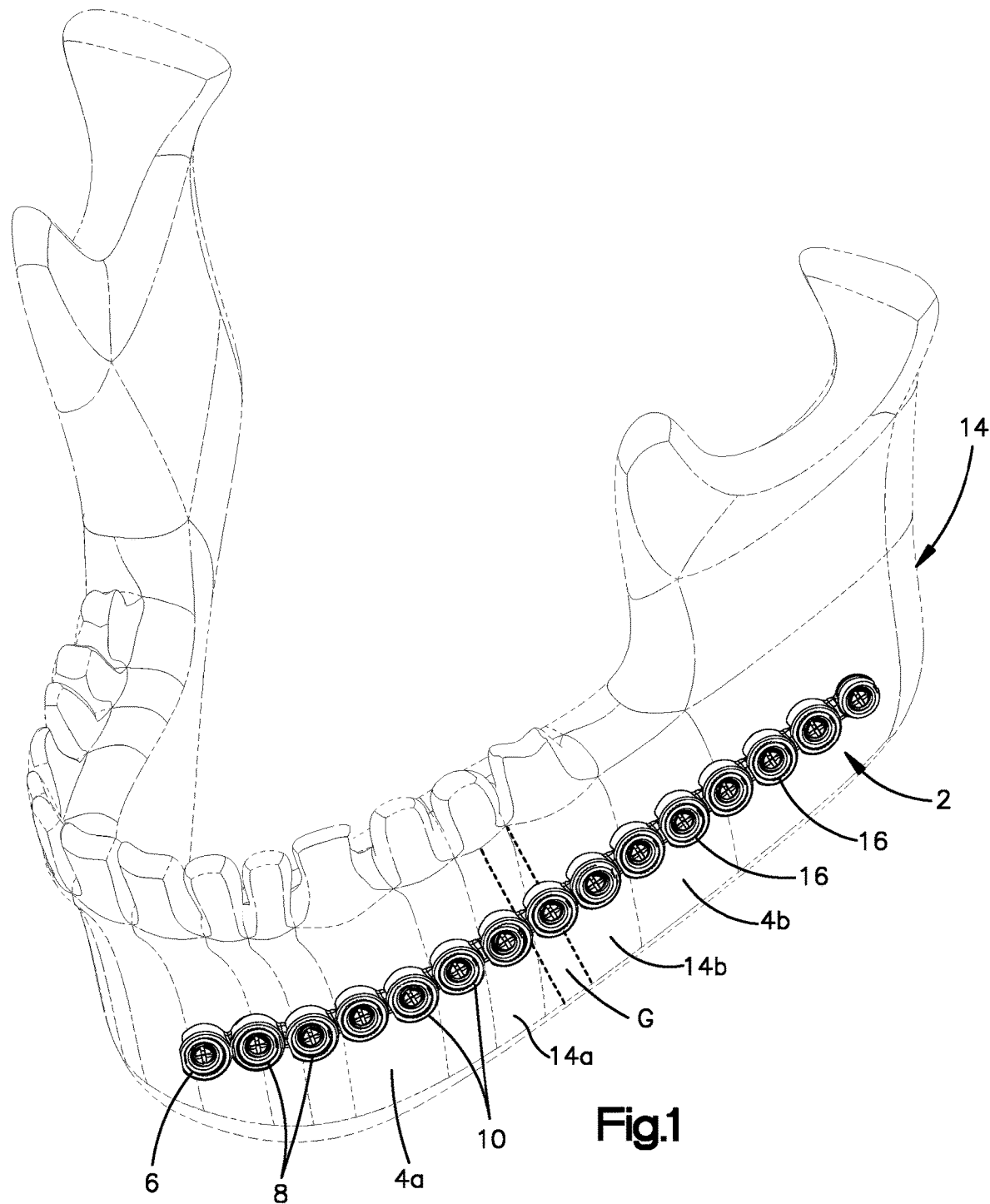
FIG. 1 is a perspective view of a bone fixation system including a bone fixation linkage and a plurality of bone anchors, shown implanted onto a target bone, according to an embodiment of the present disclosure.

Referring to FIG. 1, a bone fixation system 2 is configured to be implanted onto bone so as to stabilize a first anatomical structure 4a with respect to at least a second anatomical structure 4b so as to promote bone healing. In particular, the bone fixation system 2 can include a bone fixation linkage 6 that defines a plurality of fixation holes 8, which can be bone fixation holes configured to receive a plurality of locking members 10, such as bone anchors, preferably locking bone screws, that are configured to be driven through respective ones of the fixation holes 8 and into a respective one of the first and second anatomical structures 4a and 4b, until respective heads of the bone anchors 10 engage the bone fixation linkage 6, thereby securing the bone fixation linkage 6 to the first and second anatomical structures 4a and 4b. Thus, the bone fixation system 2 can include at least one bone fixation linkage 6 and at least one locking member 10 such as a plurality of bone anchors.

The first anatomical structure 4a can be configured as a bone or bone fragment 14a as illustrated. The term "bone" can be used to refer collectively to bone or a bone fragment. The second anatomical structure 4b can be configured as another bone fragment 14b, separated by a bone gap G, for instance when a bone is fractured, or when an osteotomy is performed on a bone. The second anatomical structure 4b can also be another bone fragment when a bone is resectioned so as to define a bone gap that separates the first and second bone fragments. Alternatively or additionally, the bone fixation system 2 is configured to stabilize the first anatomical structure with respect to a bone implant, which can be an artificial implant or a bone graft. In one example, the bone graft can be placed in the bone gap, for instance after resection. Thus, the second anatomical structure 4b can be configured as an implant, or the bone fixation system 2 can be configured to stabilize the first and second anatomical structures 4a and 4b relative to each other as described above, and further relative to a third anatomical structure, which can be bone or a bone implant. It should be appreciated, of course, that the bone fixation system 2 can be configured to stabilize any number of anatomical structures relative to each other as desired. For instance, the fractured bone can be comminuted, and thus include any number of bone fragments that can be secured relative to each other by the bone fixation system 2. Otherwise stated, the bone fixation system 2 can be configured to be implanted onto bone so as to stabilize the bone with respect to one or more other anatomical structures. Although the bone 14 is illustrated as a mandible in FIG. 1, it should be appreciated that the bone can be defined by any suitable bone as desired in the human body, or other animal body, as desired, such as the pelvis, scapula, clavicle, wrist, spine, and the thorax region, including one or more ribs, the sternum, or the like.

Referring now to FIGS. 2A and 2B, the bone fixation linkage 6 is modular, and includes a plurality of interconnected links 16, at least two of which, such as a first link 16a and a second link 16b, for example, can be pivotally connected to each other and thus configured to be attached to each other so as to angulate with respect to each other about at least one axis. Accordingly, the bone fixation linkage 6 is configured to conform to the outer contour of the first and second anatomical structures 4a and 4b to which the bone fixation linkage 6 is secured, as shown in FIG. 1.

The bone fixation linkage 6, and thus each of the links 16, can define a bottom side or first side 18a, which can define a first or bone-facing surface 20a that is configured to face the underlying anatomical structure, such as the bone 14, and a top side or second side 18b opposite the bottom side 18a. The second side 18b can define a second surface 20b that is opposite the first surface 20a. The first side 18a can be said to be spaced from the second side 18b along an inward direction, meaning a direction extending toward the underlying anatomical structure (e.g., bone). Similarly, the second side 18b can be said to be spaced from the first side 18a along an outward direction, meaning a direction extending away from underlying anatomical structure (e.g., bone).

Each of the first and second sides 18a and 18b can be sized and shaped as desired, and can define any number of surfaces as desired, including at least one or more surfaces in addition to the first and second surfaces 20a, 20b.

Figure 3A:
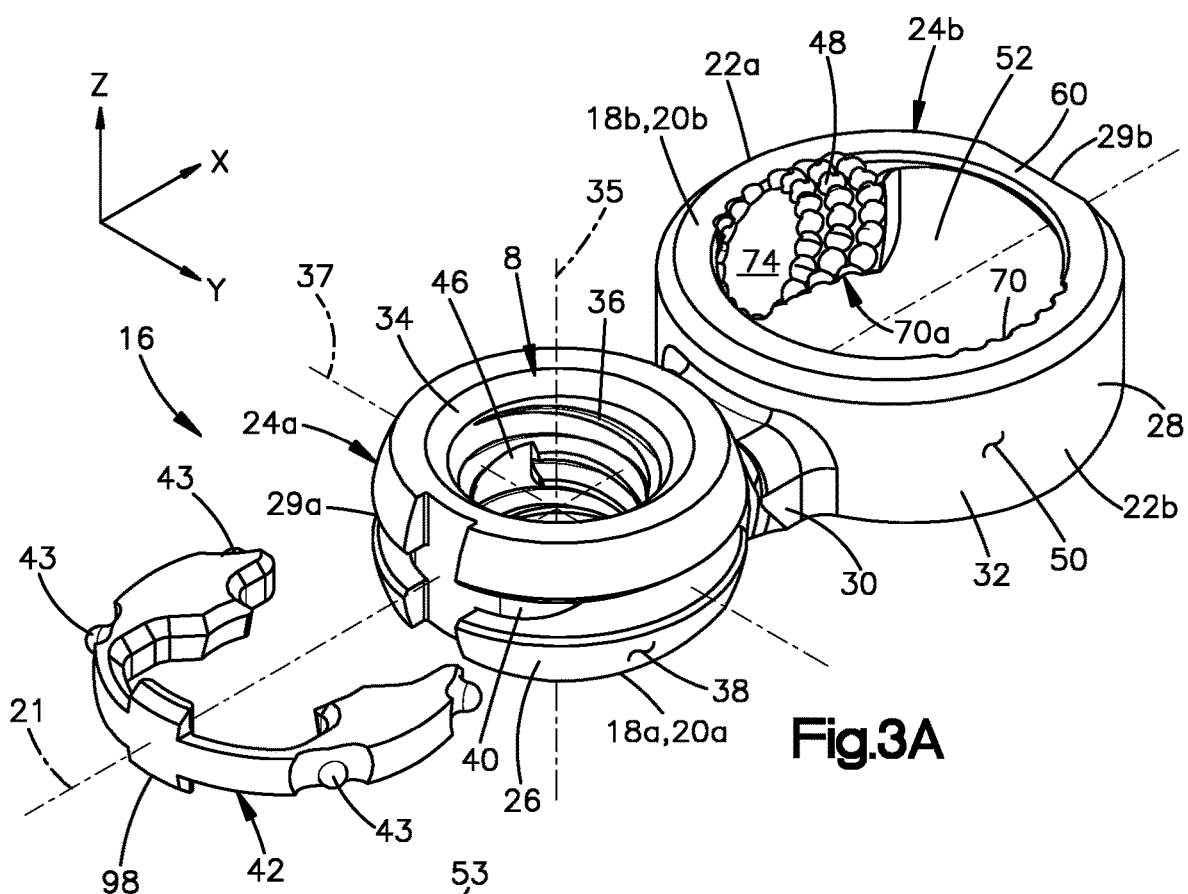
FIG. 3A is an exploded perspective view of a link assembly that includes one of the links illustrated in FIG. 2A, the link including an insertion member and a receptacle member.
Figure 3B:
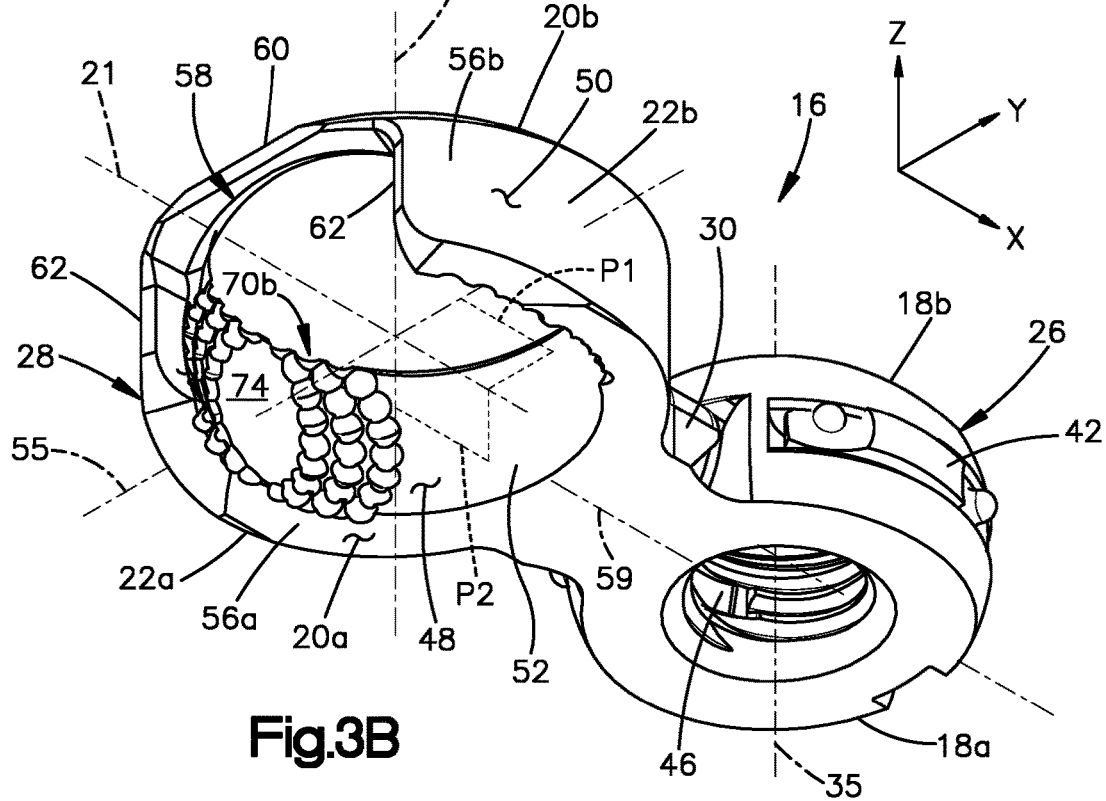
FIG. 3B is a perspective view of the link assembly illustrated in FIG. 3A.

Referring now to FIGS. 3A and 3B, each link 16 can be elongate along a first or longitudinal direction X. Each link 16 can define a longitudinal axis 21 oriented along the longitudinal direction X. The link 16 can define opposed sides 22a, 22b that are spaced from each other along a second direction, which can be referred to as a lateral direction Y, that is substantially perpendicular to the longitudinal direction X. Thus, the opposed sides 22a, 22b can be referred to as "lateral" sides of the link 16. The lateral sides 22a, 22b can each extend between the first and second sides 18a, 18b, and thus between the first and second surfaces 20a, 20b. The first and second sides 18a, 18b, and thus the first and second surfaces 20a, 20b, are spaced from each other along a third direction, which can be referred to as a transverse direction Z, that is substantially perpendicular to the longitudinal direction X and the lateral direction Y. It is to be appreciated that the inward and outward directions are each mono-directional components of the transverse direction Z, which is bi-directional.

Each link 16 can include at least a first attachment member 24a and a second attachment member 24b that are configured to attach to each other such that one of the first and second attachment members 24a, 24b of a first one of the links 16a is attached to, for instance captured by, a complementary one of the first and second attachment members 24a, 24b of a second one of the links 16b so as to define an articulating joint. Thus, the first and second links 16a, 16b can angulate with respect to each other about at least one axis. The first attachment member 24a can define an insertion member 26. The second attachment member 24b can define a receptacle member 28. The insertion member 26 and the receptacle member 28 can of a link 16 spaced from each other along the longitudinal direction X. The insertion member 26 of a link 16 can be said to extend forward from the receptacle member 28 of the link 16 along the longitudinal direction X. Thus, the insertion member 26 can define a leading end 29a of the link 16. The receptacle member 28 can be said to extend rearward from the insertion member 26 along the longitudinal direction X. Thus, the receptacle member 28 can define a trailing end 29b of the link 16.

The bone fixation linkage 6 can include any number of links 16 as desired depending on at least one of several factors, including on the desired length of the bone fixation linkage 6, the desired maneuverability of the bone fixation linkage 6, and the desired geometrical shape of the bone fixation linkage 6. In this regard, it should be appreciated that the links 16 can be attached to each other in any manner as desired such that the bone fixation linkage 6 defines any size and shape so as to conform to the underlying anatomical structure, such as underlying bone, which can be any suitable bone as desired, for instance one or more bones of the hand or the distal radius, among others, including those listed above.

Additionally, it should be appreciated that the bone fixation linkage 6 can be configured to join two different types of bone plates. For instance, the bone fixation linkage 6 can connect to a hand bone plate at one end, and to a distal radius bone plate at another end. In accordance with one embodiment, the outermost links 16 of the bone fixation linkage 6 can define outermost insertion members that are configured to be inserted into respective bone screw holes of the first and second bone plates, which can thus define receptacle members, in accordance with any embodiment described herein with respect to insertion and securement of the insertion members 26 into the receptacle members 28. Thus, the hand plate and the distal radius plate can be referred to as "links" that are configured to attach to the links 16 in the manner described herein.

Furthermore, it should be appreciated that the links 16 of the bone fixation linkage 6 can be substantially identical to each other. Thus, it can be said that each link 16 is configured to interconnect with one or more similarly configured links 16 so as to form the linkage 6 for affixation to an underlying anatomy. In other embodiments one or more and up to all of the links 16 can be constructed in accordance with alternative embodiments with respect to one or more other ones of the links 16, as is described in more detail below.

In accordance with one embodiment, each link 16 can include a neck 30 that extends between the pair of attachment members 24a, 24b, for instance from the first attachment member 24a to the second attachment member 24b. Each link 16 can include a monolithic link body 32 that includes the neck 30 and the attachment members 24a, 24b, such as the insertion member 26 and the receptacle member 28. Each link 16 can be made from any suitable biocompatible material, including a metal such as titanium, stainless steel, or alloys thereof, such as a titanium-aluminum-niobium ("TAN") alloy, or any suitable alternative implantable material, such as polymers based materials like poly-ether-ether-ketone (PEEK), or PEKK as desired.

Either or both of the attachment members 24a, 24b of one or more and up to all of the links 16 can be configured as an insertion member 26, and either or both of the attachment members 24a, 24b of one or more and up to all of the links 16 can be configured as a receptacle member 28 that is configured to capture the insertion member 26 so as to define the articulating joint. For instance, the link 16 illustrated in FIGS. 3A and 3B includes an insertion member 26 and a receptacle member 28, and thus each link 16 of this type can define and be employed as either or both of a first link 16a and a second link 16b in a linkage 6, depending on the particular joint being referenced. It should be appreciated unless otherwise indicated, that reference throughout this disclosure to first and second links 16a, 16b is intended to refer to the first link 16a whose insertion member 26 is configured to be received, or is in fact received, by the receptacle member 28 of the second link 16b to define an articulating joint.

The insertion member 26 includes an interior surface 34 that defines an opening, such as the fixation hole 8, that extends from the first side 18a to the second side 18b along a central hole axis 35. The central hole axis 35 is preferably oriented along the transverse direction Z. Thus, in such embodiments, the central hole axis 35 can be referred to as a transverse axis. Moreover, in such embodiments, with reference to angulation between the first and second links 16a, 16b, the central hole axis 35 can be referred to as the transverse axis of the first link 16a. The fixation hole can also define a lateral hole axis 37 that is oriented along the lateral direction Y. Preferably, the lateral hole axis 37 of a link 16 intersects the longitudinal axis 21 and the central hole axis 35 of the link 16. In such embodiments, with reference to angulation between the first and second links 16a, 16b, the lateral hole axis 37 can be referred to as the lateral axis of the first link 16a. The fixation hole 8 is configured to receive a respective one of the locking members 10, such as a bone screw, for example. The interior surface 34 can include projections such as internal threads 36 that threadedly purchase with complementary external threads on the head of a locking member 10. The insertion member 26 further include an exterior surface 38 that is opposite the interior surface 34 so as to at least partially surround the fixation hole 8. The exterior surface 38 of the insertion member 26 is configured to reside within, and angulate within, the receptacle member 28 of a second link 16b. The exterior surface 38 preferably has a spherical geometry, such as defining one or more portions or segments of a sphere, which facilitates angulation of the insertion member 26 within the receptacle member 28.

The exterior surface 38 defines a recess 40, such as an annular groove or channel, that is configured to receive a retention member 42, such as a flexible retention clip, preferably a C-clip, for example. Thus, the retention clip 42 can be referred to as a "retention clip." The retention clip 42 includes at least one retention feature, such as a "male" retention feature, such as at least one protrusion 43, that is configured to engage a complementary retention structure of the receptacle member 28, which retention structure includes a plurality of complimentary retention features, such as "female" retention features, as described in more detail below. The insertion member 26 can define a second recess, such as a notch 44, that is configured to receive a rib 98 of the retention clip 42 for maintaining an angular position between the retention clip 42 and the insertion member 26 about the central hole axis 35. The notch 44 preferably extends along the transverse direction Z and is in communication with the recess 40. For example, the notch 44 can extend downwardly from the recess 40 toward the first surface 20a of the link 16 and/or upwardly from the recess 40 toward the second surface 20b of the link 16. Preferably, the notch 44 extends both downwardly and upwardly from the recess 40 toward both of the first surface 20a and second surface 20b of the link 16. The notch 44 can be aligned with the longitudinal axis 21 of the link 16 along the transverse direction Z. The insertion member 26 defines at least one opening 46 that extends from the recess 40 to the fixation hole. Thus, the fixation hole 8 and the recess 40 are in communication with one another via the at least one opening 46. Preferably, the at least one opening 46 includes a pair of openings 46 each extending internally from the recess 40 to the fixation hole 8. Thus, the at least one opening 46 can be said to extend externally from the fixation hole 8 to the recess 40. The pair of openings 46 can be spaced from each other along the lateral direction Y, although other opening 46 arrangements are within the scope of the present disclosure.

The receptacle member 28 includes an interior surface 48 and an exterior surface 50 opposite the interior surface 48. The interior surface 48 defines a receptacle 52 sized and configured to receive at least a portion, such as substantially all, of the exterior surface 38 of the insertion member 26. For instance, the interior surface 48 can be sized and configured to capture the exterior surface 38 of the insertion member 26 when the insertion member 26 is received in the receptacle 52. The exterior surface 38 of the insertion member 26 is preferably configured to engage, such as by riding along, the interior surface 48 of the receptacle 52 as the corresponding links 16 angulate with respect to each other. The interior surface 48 preferably has a spherical geometry, such as defining one or more portions or segments of a sphere, which is complementary of the spherical geometry of the exterior surface 38 of the insertion member 26, thereby facilitating angulation between the insertion member 26 of a first link 16a and the receptacle member 28 of a second, interconnected link 16 about one or multiple axes. Thus, engagement between the exterior surface 38 of the insertion member 26 and the interior surface 48 of the receptacle member 28 can be referred to as a "spherical joint," which provides a linkage 6 comprising the first and second links 16a, 16b with poly-axial adaptability in each of the longitudinal, lateral, and transverse directions X, Y, Z, as described in more detail below.

The receptacle 52 can extend from the first side 18a to the second side 18b of the link 16 along a central receptacle axis 53. The central receptacle axis 53 is preferably oriented along the transverse direction Z. Thus, in such embodiments, the central receptacle axis 53 can be referred to as a transverse axis. Moreover, in such embodiments, with reference to angulation between the first and second links 16a, 16b, the central receptacle axis 53 can be referred to as the transverse axis of the second link 16b. The central receptacle axis 53 of a link 16 is preferably aligned with the central hole axis 35 of the link 16 along the longitudinal direction X. Preferably, the longitudinal axis 21 of the link 16 intersects each of the central hole axis 35 and the central receptacle axis 53. When the insertion member 26 of the first link 16a resides within the receptacle 52 of the second link 16b, the central hole axis 35 of the first link 16a is preferably coincident with the central receptacle axis 53 of the second link 16b when the links 16a, 16b are in a neutral un-angulated position. The receptacle 52 can also define a lateral receptacle axis 55 that is oriented along the lateral direction Y. In such embodiments, with reference to angulation between the first and second links 16a, 16b, the lateral receptacle axis 55 can be referred to as the lateral axis of the second link 16b. The lateral receptacle axis 55 of a link 16 preferably intersects each of the central receptacle axis 53 and the longitudinal axis 21 of the link 16. The neck 30 can extend from the exterior surface 38 of the insertion member 26 to the exterior surface 50 of the receptacle member 28. The neck 30 can be straight or curved as desired. The neck 30 can define a central axis 59 that extends from the insertion member 26 to the receptacle member 28, and in particular extends along the longitudinal direction X and intersects the central hole axis 35 and central aperture axis 53 of the link 16.

The longitudinal axis 21 and the lateral receptacle axis 55 of each link 16 can define a first or primary reference plane P1, such that angulation of at least one or more and up to all of the links 16 with respect to another one of the links 16, for instance an adjacent one of the links 16, within or along the primary reference plane P1 can be referred to as "in-plane" angulation. Angulation of at least one or more up to all of the links 16 with respect to another one of the links 16, for instance an adjacent one of the links 16, along a direction that intersects the plane, and thus has a directional component in the transverse direction Z, can be referred to as "out-of-plane" angulation. Further, at least one or more up to all of the links 16 can angulate torsionally with respect to another one of the links 16, for instance an adjacent one of the links 16, about the longitudinal axis 21. As will be described in more detail below, the links 16 can be configured to angulate with respect to each other in-plane, out-of-plane, torsionally, or a combination of two or more and up to all thereof. In-plane angulation can cause the links 16 to move in a direction that is substantially parallel or tangential to the underlying anatomical structure. Out-of-plane angulation can cause the links 16 to move in a direction toward or away from the underlying anatomical structure.

The exterior surface 50 of the receptacle member 28 can have a curved geometry, such as a cylindrical geometry, for example. The receptacle member 28 can further include at least one arm that defines at least a portion of the interior surface 48 and the exterior surface 50, such that the neck of the first link 16a extends past the at least one arm. The at least one arm can be curved or otherwise shaped as desired. For instance, the receptacle member can define a pair of arms, such as first and second arms 56a, 56b, that each define at least a portion of the interior surface 48 and the exterior surface 50. The first and second arms 56a, 56b can extend away from the insertion member 26 of the link 16. It is to be appreciated that the receptacle member 28 can include any number of arms 56a, 56b as desired. The arms 56a, 56b can be spaced from each other so as to define a channel 58 that separates the first and second arms 56a, 56b, such that the at least a portion of the neck 30 of the first link 16a extends through the channel 58 when the insertion member 26 of the first link 16a is captured by the receptacle member 28 of the second link 16b. Further, the channel 58 can further be sized such that interference between the receptacle member 28 and the neck 30 of the first link 16a limits certain angular movements of the first and second links 16a, 16b with respect to each other. For example, the channel 58 can define a width in the lateral direction Y that is greater than the width of the neck 30 of the insertion member 26 at a location where the neck 30 is disposed in the channel 58. Thus, the first link 16a is configured to angulate with respect to the second link 16b until the neck 30 of the first link 16a abuts a respective one of the arms 56a, 56b that defines the channel 58, at least when the neck 30 of the first link 16a resides within the channel 58.

The receptacle member 28 can further include a bridge 60 that interconnects the first and second arms 56a, 56b. The bridge 60 can extend across the channel 58 from a trailing end 62 of the first arm 56a to a trailing end 62 of the second arm 56b, such that the channel 58 extends from one of the first and second sides 18a and 18b to the bridge 60. The bridge 60 can define a portion of the interior surface 48 and a portion of the exterior surface 50, and can thus partially define the receptacle 52. In accordance with one embodiment, the exterior surface 50 can be convex at the bridge 60 along a plane defined by the lateral direction Y and the longitudinal direction X. In accordance with the illustrated embodiment, the bridge 60 is disposed at the second side 18b of the link 16, such that the channel 58 extends from the first side 18a to the bridge 60. Thus, it can be said that the link 16, particularly the receptacle member 28, defines the channel 58, which extends between the pair of arms 56a, 56b along the lateral direction Y and from the first surface 20a to the bridge 60 along the transverse direction Z. Accordingly, the insertion member 26 is configured to be inserted into the receptacle 52 along a direction having at least a directional component from the first end 18a toward the second end 18b. Additionally, the channel 58 can be said to be "in-line" with the longitudinal direction X, such that the longitudinal axis 21 of the link 16 extends equidistantly between the trailing ends 62 of the arms 56a, 56b with respect to the lateral direction Y.

The first and second links 16a, 16b can be coupled to one another according to one example method as follows: with the first and second links 16a, 16b remote from each other, the first link 16a can be oriented perpendicularly out-of-plane with respect to the second link 16b (i.e., the longitudinal axes 21 of the first and second links 16a, 16b are oriented at 90 degrees to each other in the secondary reference plane P2), the first link 16a can also be rotated so as to be torsionally offset from the second link 16b by 90 degrees (i.e., the first link 16a is rotated 90 degrees about its longitudinal axis 21), at this orientation, the insertion member 26 of the first link 16a can be advanced into the receptacle 52 of the second link 16b in a direction along the longitudinal axis 21 of the first link 16. Once inserted in this manner, the first link 16a can then be angulated toward in-plane alignment (i.e., so that the second surface 18b of the first link 16a moves toward the second surface 18b of the second link 16b) and torsionally returned toward in-plane alignment with the second link 16b until the insertion member 26 of the first link 16a is captured within the receptacle 52 of the second link 16b (i.e., exterior surface 38 of the first link 16a is captured between interior surface 48 along the arms 56a, 56b of the second link 16b). In other example methods, the insertion member 26 of the first link 16a can be inserted into the receptacle 52 of the second link 16b along a direction having at least a directional component along the longitudinal direction, particularly when the first link 16a is torsionally out-of-plane relative to the second link 16b during insertion. It is to be appreciated that the first and second links 16a, 16b can be coupled together outside of a patient or in situ, as necessary.

At least a portion up to an entirety of the neck 30 of the first link 16a can be spaced from the second surface 20b along the transverse direction Z a distance at least substantially equal to the thickness of the bridge 60 of the second link 16b along the transverse direction Z, such that the bridge 60 of the second link 16b does not mechanically interfere with the neck 30 of the first link 16a when the insertion member 26 is disposed in the receptacle member 28 and the respective central hole and receptacle axes 35, 53 are parallel with each other. Additionally, the trailing ends 62 of the first and second arms 56a, 56b can converge towards one another so as to inhibit, such as by mechanical interference, withdrawal of the insertion member 26 of the first link 16a from the receptacle 52 of the second link 16b (or insertion of the insertion member 26 into the receptacle 52) at least along the longitudinal direction X. It should be appreciated that the bridge 62 can define any geometric shape as desired. With reference to the illustrated embodiment, with the bridge 60 disposed at the second side 18b of the link 16, the second link 16b can optionally be attached to the first link 16a and/or removed from the first link 16a in situ. In accordance with an alternative embodiment, the bridge 60 can be disposed at or adjacent the first side 18a of the link 16, such that the bridge 60 is spaced from the second side 18b along the transverse direction Z. Accordingly, the first link 16a can optionally be attached to the second link 16b and removed from the second link 16b in situ.

The interior surface 48 of the receptacle member 28 can include a retention structure for retaining or otherwise affixing relative positions between the insertion member 26 of the first link 16a and the receptacle member 16 of the second link 16b, and thus also the relative positions between the first link 16a and the second link 16b. The retention structure can be defined by the interior surface 48, such as by the one or both of the arms 56a, 56b, for example. The retention structure can include at least one array 70 of female retention features, such as recesses or dimples 72, which array 70 is also referred to herein as a "dimple array." Each of the dimples 72 can define a geometry, such as a spherical geometry, such as one or more portions or segments of a sphere, which is configured to receive a complimentary geometry of at least one protrusion 43 extending from the retention clip 42. It is to be appreciated, however, that the dimples 72 and the at least one protrusion can define other complimentary geometries, such as spheroidal, pyramid, conical, cuboid, or frustum geometries (including a frustum of any of the foregoing geometries), by way of non-limiting examples. When such alternative geometries are employed, they preferably include edges that are radiused, beveled, chamfered, or otherwise blunted. It is also to be appreciated that, in additional embodiments, one or more dimples of the at least one array 70 can have a geometry that is different than one or more other dimples of the at least one array 70. For example, the at least one array 70 can employ dimples 70 of various geometries. Additionally, the retention clip 42 can employ protrusions 43 of various respective geometries. In the illustrated embodiments, the at least one dimple array 70 includes a first dimple array 70a and a second dimple array 70b spaced from each other on the interior surface 48 along the lateral direction Y. Each dimple 72 of each array 70, such as the first and second dimple arrays 70a, 70b, is preferably configured to receive the at least one protrusion 43 of the retention clip 42. Each dimple array 70a, 70b can be arranged around, or at least partially around, a central surface, such as a pivot or bearing surface 74 that preferably is substantially smooth.

Figure 3C:
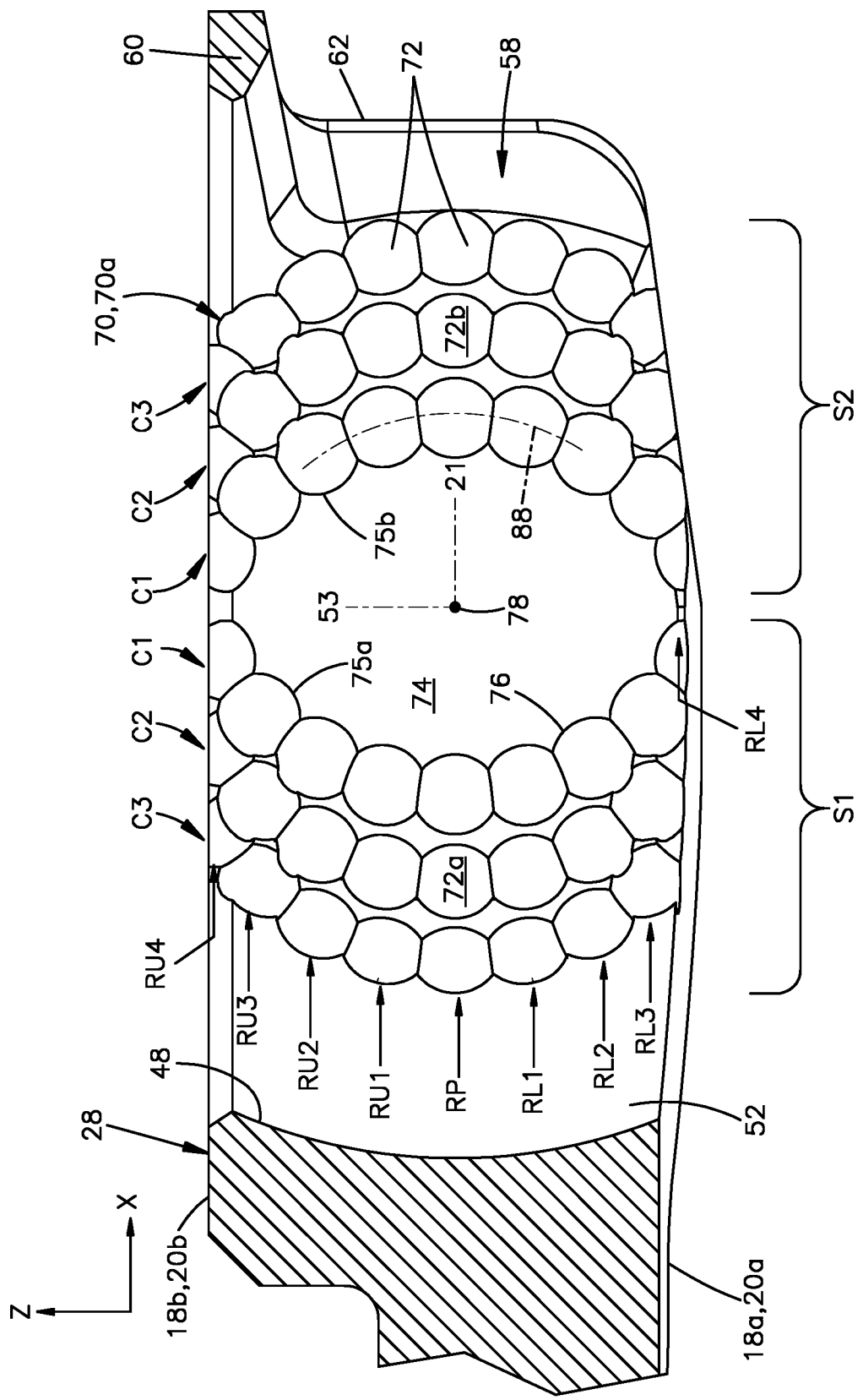
FIG. 3C is an elevation view of an interior surface of the receptacle member illustrated in FIG. 3A.

Referring now to FIG. 3C, the bearing surface 74 can have a generally round profile, such as a circular or elliptical profile, as viewed from a second or secondary reference plane P2 containing the longitudinal and central receptacle axes 21, 53. In the illustrated embodiment, the bearing surface 74 profile can be said to be football-shaped, with the tips of the football aligned along the transverse direction Z. A periphery 76 of each bearing surface 74 can be at least partially bounded by the respective dimple array 70. The bearing surface 74 can define a portion of the spherical geometry of the interior surface 48. Stated differently, the bearing surface 74 can be a portion of the interior surface 48 that is devoid of dimples 72. Alternatively, the bearing surface 74 can define a boss that extends internally from the interior surface 48 toward the central receptacle axis 53. Preferably, the lateral receptacle axis 55 intersects each bearing surface 74 at its centerpoint 78 with respect to both of the longitudinal and transverse directions X, Z. Additionally, each bearing surface 74 is preferably substantially normal to the lateral receptacle axis 55 at the centerpoint 78.

Each dimple array 70 can be arranged in rows R and columns C of dimples 72 spaced around the bearing surface 74. Each row R of dimples preferably extends annularly along the interior surface 48 along a single plane that is parallel with the primary reference plane. In the illustrated embodiments, each dimple array 70 can include one or more sets S of dimples, such as a first or leading set S1 of dimples, arranged in rows R and columns C of dimples, on a leading side 75a of the bearing surface 74 and a second or trailing set S2 of dimples, arranged in rows R and columns C of dimples, on a trailing side 75b of the bearing surface 74. Each of the first and second sets S1, S2 of dimples 72 can include an innermost column C1, one or more intermediate columns C2, and an outermost column C3 of dimples. In the illustrated embodiment, each of the first and second sets S1, S2 of dimples 72 has a single intermediate column C2 of dimples 72. It is to be appreciated, however, that fewer or more columns C of dimples 72 can be employed as needed, such as more intermediate columns C2, for example.

As viewed from the secondary reference plane, each column C of dimples can follow a path 88 that is curved and substantially follows the respective peripheral leading or trailing side 75a, 75b of the associated bearing surface 74. Thus, the path 88 of each column C is preferably semicircular or semi-elliptical, or at least substantially so, when viewed from the secondary reference plane P2. With respect to each dimple array 70: the innermost columns C1 of the first and second sets S1, S2 can be referred to as a pair of innermost columns C1; the one or more intermediate columns C2 of the first and second sets S1, S2 can be referred to as a pair or respective pairs of intermediate columns C2; and the outermost columns C3 of the first and second sets S1, S2 can be referred to as a pair of outermost columns C3. Each pair of innermost columns C1, intermediate columns C2, and outermost columns C3 can be said to complimentarily define an orbital or orbital-like pattern around the associated bearing surface 74. As illustrated, the columns C of dimples in each set S1, S2 can converge toward each other proximate the second surface 20b of the receptacle member 28. In such embodiments, at least one or more of the dimples 72 can merge with one or more other dimples 72 of the array 70 increasingly from the first surface 20a toward the second surface 20b.

As shown in the illustrated embodiment, each of the first and second sets S1, S2 of dimples of each array 70 can include: a primary row RP of dimples that is preferably located along the primary reference plane; a first lower row RL1 of dimples spaced between the primary row RP and the first surface 20a of the link 16; a second lower row RL2 of dimples spaced between the first lower row RL1 and the first surface 20a; a third lower row RL3 of dimples spaced between the second lower row RL2 and the first surface 20a; and at least a portion of a fourth lower row RL4 of dimples spaced between at least a portion of the third lower row RL3 and the first surface 20a. Each of the first and second sets S1, S2 of dimples of each array 70 can include: a first upper row RU1 of dimples spaced between the primary row RP and the second surface 20a of the link 16; a second upper row RU2 of dimples spaced between the first upper row RU1 and the second surface 20b; a third upper row RU3 of dimples spaced between the second upper row RU2 and the second surface 20b; and at least a portion of a fourth upper row RU4 of dimples spaced between at least a portion of the third upper row RU3 and the second surface 30b. In the illustrated embodiment, the fourth lower row RL4 and the fourth upper row RU4 of dimples can each be referred to as an outermost row of dimples. It is to be appreciated, however, that each of the first and second sets S1, S2 of dimples of each array 70 can include fewer or more rows R of dimples as needed. In each dimple array 70, the first lower row RL1, second lower row RL2, third lower row RL3, fourth lower row RL4, first upper row RU1, second upper row RU2, third upper row RU3, and fourth upper row RU4 of dimples of one set S1, S2 can be coplanar with its counterpart row in the other set S1, S2 of rows R and columns C of dimples, as well as with their counterparts in each other dimple array 70.

Each dimple 72 in the interior surface 48 of the receptacle member 28 can be uniquely identified by the array 70, set S, row R, and column C in which it is located. With reference to the illustrated embodiment, in each set S of each array 70, the dimple 72 of the primary row RP and intermediate column C2 can be referred to as a "neutral" dimple 72. Accordingly, the dimple 72a of the primary row RP and intermediate column C2 of the first set S1 can be referred to as the "leading neutral dimple", while the dimple 72b of the primary row RP and intermediate column C2 of the second set S2 can be referred to as the "trailing neutral dimple." The neutral dimples 72a, 72b of each array 70 are configured to receive a respective protrusion 43 of the retention clip 42, such as the first and second protrusions 43a, 43b, respectively, of the first clip arm 92a, or the third and fourth protrusions 43c, 43d, respectively, of the second clip arm 92b, when the first and second links 16a, 16b are in a neutral, un-angulated position, as described in more detail below.

At least some and preferably all of the dimples 72 are configured to selectively receive one or more protrusions 43 extending in an external direction from the retention clip 42 so as to retain or otherwise affix relative positions between the insertion member 26 of the first link 16a and the receptacle member 16 of the second link 16b, as described in more detail below. It is to be appreciated that dimple arrangements other than those set forth above are within the scope of the present disclosure.

Referring now to FIGS. 4A through 4E, the retention clip 42 can have a generally U-shaped body 90 that includes a pair of clip arms 92a, 92b and a connecting portion 94 that may permit the clip arms 92a, 92b to flex elastically toward and away from each other as needed. The clip arms 91a, 92b are also configured to transmit a force, such as a locking force, that affixes the relative position between the first and second links 16a, 16b, such as when the locking member 10 is fully seated within the respective fixation hole 8. The locking force is preferably exerted in an external direction, such as a radial direction R1 away from and perpendicular to the central hole axis 35 when the retention clip 42 resides within the recess 40. The locking force, as well as the mechanism by which the relative positions of the first and second links 16a, 16b are affixed, are described in more detail below. The retention clip 42 can be made from any suitable biocompatible material, including a metal such as titanium, stainless steel, or alloys thereof, such as a TAN alloy, or other alloys such as cobalt-chromium-nickel alloy (such as elgiloy), or any suitable alternative implantable material, such as polymers based materials like poly-ether-ether-ketone (PEEK), or PEKK as desired.

The retention clip 42 can define a first clip surface 96a configured to face toward the underlying anatomy and an opposed second clip surface 96b configured to face away from the underlying anatomy when the retention clip 42 resides within the recess 40. One or both of the first and second clip surfaces 96a, 96b can be substantially planar, although other geometries are within the scope of the present disclosure. The retention clip 42 can define a rib 98 that is configured to reside within the notch 44 of the insertion member so as to maintain the angular position between the retention clip 42 and the insertion member 26 about the central hole axis 35. The rib 98 can extends inwardly from the first clip surface 96a along the transverse direction Z and/or outwardly from the second clip 96b surface along the transverse direction Z. Preferably, the rib 98 extends both inwardly from the first clip surface 96a and outwardly from the second clip surface 96b. The rib 98 can be aligned with the longitudinal axis 21 of the link 16 along the transverse direction Z. The rib 98 can define a portion of the exterior surface of the retention clip 42.

Figure 4A:
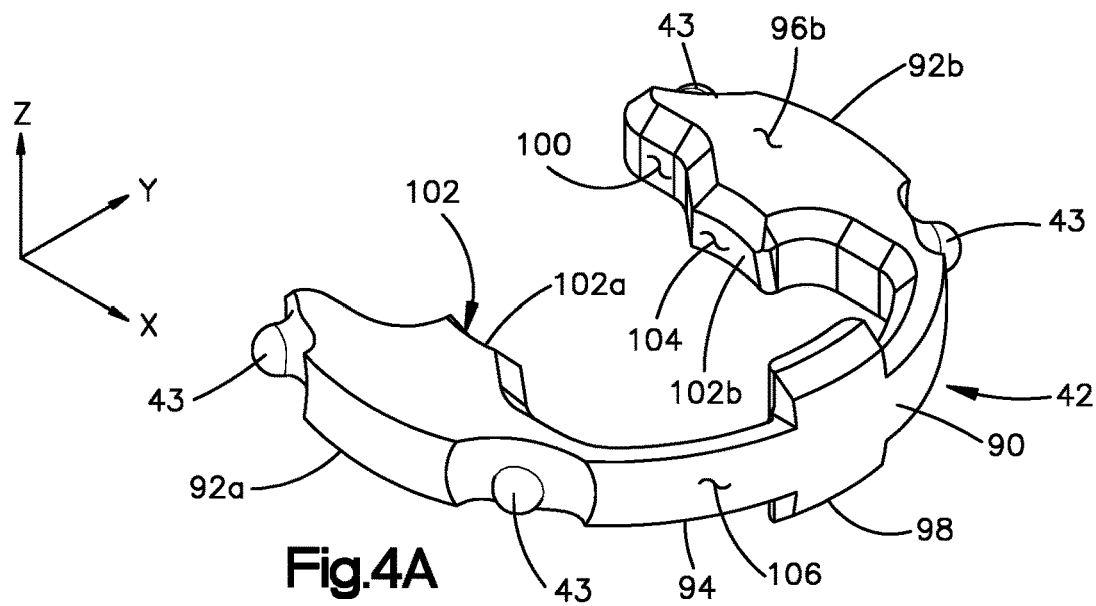
FIG. 4A is a perspective view of a retention clip of the link assembly illustrated in FIG. 3A.
Figure 4B:
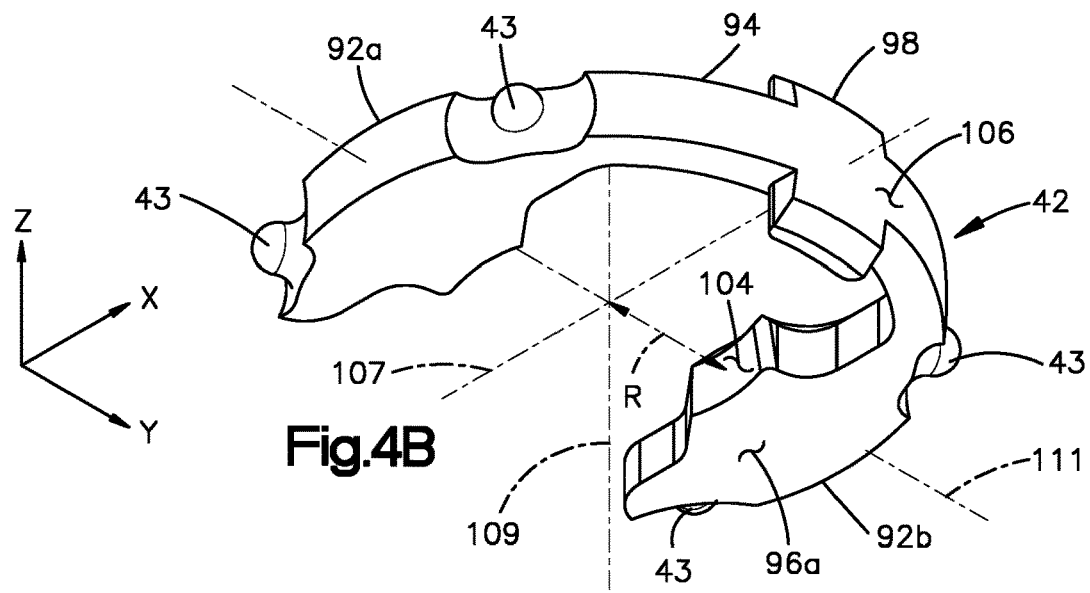
FIG. 4B is another perspective view of a retention clip illustrated in FIG. 4A.
Figure 4C:
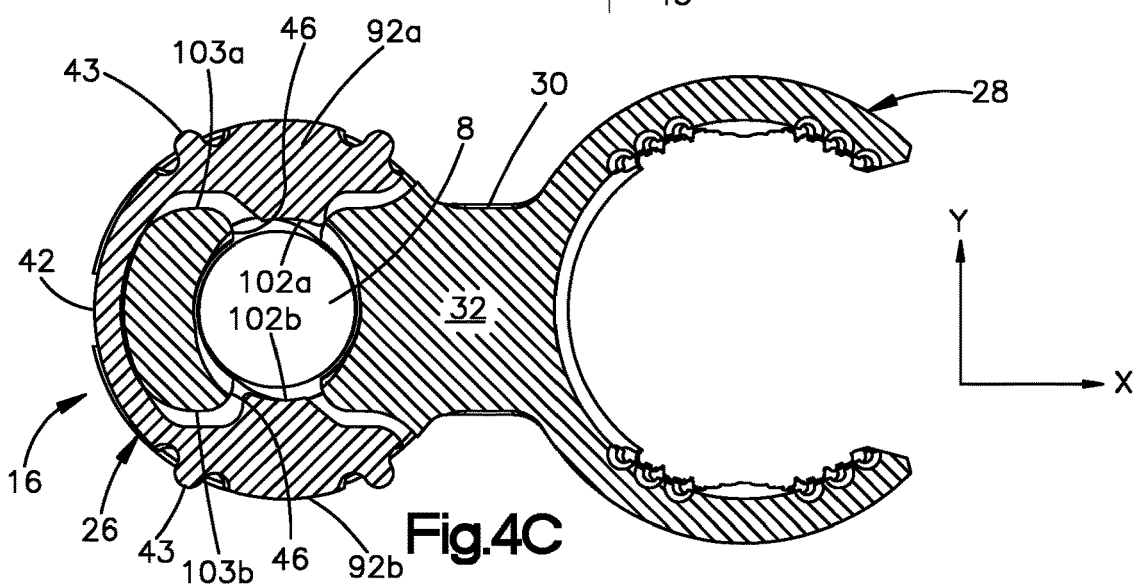
FIG. 4C is a sectional top view of the link assembly illustrated in FIG. 3B.

The retention clip 42 defines an interior surface 100 that faces generally toward the central hole axis 35 when the retention clip 42 is received within the recess 40. The interior surface 100 defines at least one projection 102 that extends toward the central hole axis 35 when the retention clip 42 resides within the recess 40. One or both of the clip arms 92a, 92b can define at least a portion of the interior surface 100 of the retention clip 42. At least one of the clip arms 92a, 92b can define the at least one projection 102. Preferably, the at least one projection 102 includes a first projection 102a on the first clip arm 92a and a second projection 102b on the second clip arm 92b. The projections 102a, 102b are configured to extend through the openings 46, respectively, and into the fixation hole 8, as shown in FIG. 4C. Each projection can define an innermost surface 104 that preferably is substantially smooth. The innermost surface 104 can define a circular profile, such as a segment or a portion of a circle, in the primary reference plane P1. In the illustrated embodiment, the innermost surfaces 104 of the first and second projections 102a, 102b can be spaced from each other so as to define an inner diameter measured along a line intersecting each surface 104 and normal to each surface 104, such as a line extending along the lateral direction Y and intersection the central hole axis 35 when the retention clip 42 in the recess 40, for example. It is to be appreciated, however, that other relative arrangements between the innermost surfaces 104 are within the scope of the present disclosure. The innermost surfaces 104 are configured to receive the locking force.

Additionally, within the recess 40, the insertion member 26 preferably defines opposed lateral portions 103a, 103b that are spaced from each other along the lateral direction Y so as to define an outer diameter that is greater than the inner diameter of surfaces 104, at least when the retention clip 42 is in a neutral or unbiased configuration. Thus, to couple the retention clip 42 to the insertion member 26, an open end of the clip 42 opposite the notch 44 can be advanced along the recess 40 in the longitudinal direction X toward the trailing end 29b, causing the innermost surfaces 104 of the projections 102a, 102b to ride along lateral portions 103a, 103b and thus causing the arms 92a, 92b to flex laterally outward and increasing inner diameter until the innermost surfaces 104 clear the lateral portions 103a, 103b, which causes the arms 92a, 92b to responsively snap or flex inward so that the projections 102a, 102b then reside in the openings 46. The geometry of one or both of the projections 102a, 102b can be configured to prevent, impede, or at least resist the retention clip 42 from backing out of the recess 40. Thus, the retention clip 42 can be said to have a "snap-fit" engagement with the insertion member 26.

The retention clip 42 defines an exterior surface 106 opposite the interior surface 100. The exterior surface 106 of the retention clip 42 preferably has a spherical geometry, such as defining one or more portions or segments of a sphere, which facilitates angulation of the retention clip 42 in unison with the insertion member 26 within the receptacle member 28. Accordingly, as viewed in the primary reference plane P1, the exterior surface 106 of the retention clip 42 can have a generally circular or semi-circular profile. One or both of the clip arms 92a, 92b can define at least a portion of the exterior surface 106. The retention clip 42 can define a longitudinal clip axis 107 and a central clip axis 109 that is offset from the longitudinal clip axis 107. In the illustrated embodiment, the central clip axis 109 is substantially perpendicular to the longitudinal clip axis 107. When the retention clip 42 resides within the recess 40, the longitudinal clip axis 107 is preferably substantially coincident with the longitudinal axis 21 of the link 16, and the central clip axis 109 is preferably substantially coincident with the central hole axis 35. The retention clip 42 also defines a lateral clip axis 111 that is oriented along the lateral direction Y and preferably intersects the central clip axis 109, and thus also preferably intersects the central hole axis 35 when the retention clip 42 resides within the recess 40. The longitudinal and lateral clip axes 107, 111 preferably extend along the primary reference plane P1 when the retention clip 42 resides within the recess 40.

Figure 4D:
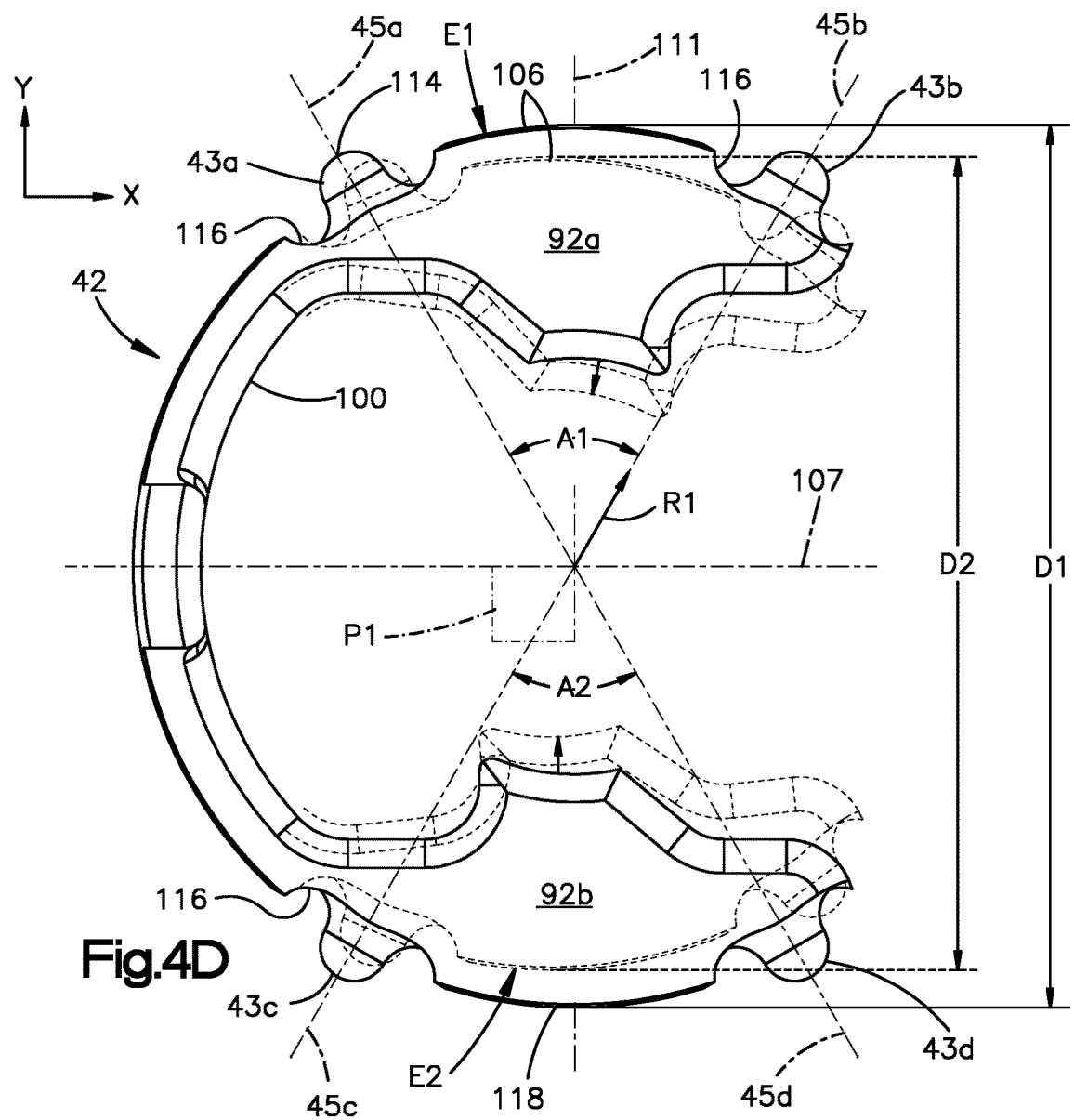
FIG. 4D is a top view of the retention clip illustrated in FIG. 4A, showing a mode of flexure of the retention clip according to an embodiment of the present disclosure.

As shown in FIG. 4D, the retention clip 42 is flexible between an initial or first, unbiased configuration E1, whereby the exterior surface 106 of the clip arms 92a, 92b define a first maximum lateral dimension, such as a first diameter D1, measured along the lateral clip axis 111, to a second, biased configuration E2, whereby the exterior surface 106 of the clip arms 92a, 92b define a second maximum dimension, such as a second diameter D2, that is measured along the lateral clip axis 111 and is less than the first diameter D1. In this manner, the retention clip 42 is flexible so that at least one of the clip arms 92a, 92b can be moved elastically toward the other clip arm 92b, 92a, and preferably so that both clip arms 92a, 92b can be moved toward each other, along the lateral direction Y.

The at least one protrusion 43 projects from (i.e., extends away from) the exterior surface 106 of the retention clip 42 in an external direction. Stated differently, the at least one protrusion 43 extends away from the central clip axis 109, and thus away from the central hole axis 35 when the retention clip 42 resides within the recess 40. When the insertion member 26 extends within the receptacle of an adjacent link 16, such as the second link 16b, the at least one protrusion 43 also extends away from the central receptacle axis 53 of the adjacent link 16. When the retention clip 42 resides in the recess 40 and is in the unbiased configuration E1, the at least one protrusion 43 extends away from the central hole axis 35 (and thus also from the central clip axis 109) at a first radial distance measured along a radial direction R1 perpendicular to the central hole axis 35. Additionally, when the retention clip 42 is in the biased configuration E2, the at least one protrusion 43 extends away from the central hole axis 35 (and thus also from the central clip axis 109) at a second radial distance that is less than the first radial distance, as measured along the radial direction R1.

The at least one protrusion 43 preferably extends externally beyond the exterior surface 38 of the associated insertion member 26, at least when the retention clip 42 is in the unbiased configuration E1, and optionally also when in the biased configuration E2. An external end of the at least one protrusion 43 can define a tip 114 having a geometry, such as a spherical geometry, such as a portion of segment of a sphere, such as a hemisphere or a portion of a hemisphere, for example.

Figure 4E:
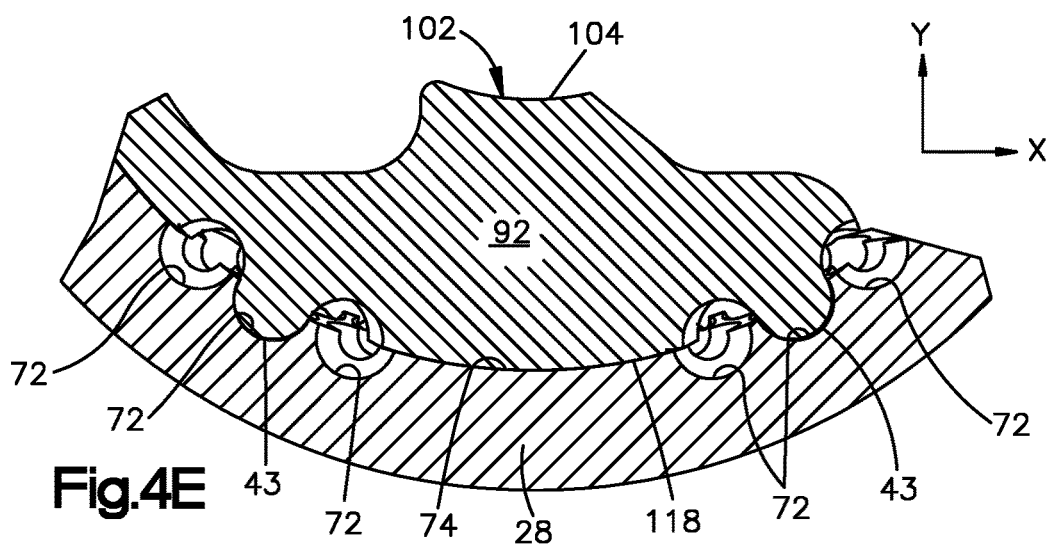
FIG. 4E is a magnified view of a portion of the retention clip illustrated in FIG. 4C, showing an external protrusion of the retention clip received within a complimentary dimple defined by an interior surface of the retention member, according to an embodiment of the present disclosure.

As shown in FIG. 4E, the geometry of the protrusion tip 114 can be complimentary with the geometry of any one of the dimples 72 so as to engage the dimple, such as by residing within or fitting snugly within the dimple 72, at least when the retention clip 42 is in the unbiased configuration E1. Thus, the at least one protrusion 43 is receivable within a respective dimple 72 when the retention clip 42 is in the unbiased configuration E1, and the at least one protrusion 43 is spaced radially inward from the respective dimple 72 when the retention clip 42 is in the biased configuration E2. In this manner, as the insertion member 26 of the first link 16a angulates within the receptacle 52 of the second link 16b, the at least one protrusion 43 rides along the respective dimple array 70, such as by riding into and out of adjacent dimples 72. The retention clip 42 flexes between the unbiased and biased configurations E1, E2 as the at least one protrusion 43 rides along and into and out of adjacent dimples 72. In the illustrated embodiment: as the protrusion 43 rides into a dimple 72, the retention clip 42 flexes from the biased configuration E2 to the unbiased configuration E1; when the protrusion 43 is fully seated in a dimple 72, the retention clip 72 is in the unbiased configuration E1; and as the protrusion rides out of a dimple 72, the retention clip 42 moves from the unbiased configuration E1 to the biased configuration E2. It is to be appreciated that the retention clip 42 can be in a third, intermediate configuration between the unbiased and biased configurations E1, E2 when the at least one protrusion 43 is fully seated in one or more of the dimples 72. The retention clip 42 can be biased while in the intermediate configuration, although less biased than when the retention clip 42 is in the biased configuration E2. It is also to be appreciated that, in other embodiments, the retention clip 42 can be configured so that its unbiased configuration coincides with when the at least one protrusion 43 is spaced radially inward from an adjacent dimple 72, and the biased configuration coincides with when the at least one protrusion is fully seated within an adjacent dimple 72, as discussed in more detail below.

Referring again to FIG. 4D, in some embodiments, the retention clip 42 can include four (4) protrusions 43a, 43b, 43c, 43d extending externally from the exterior surface 106 of the retention clip 42. One or more and up to all of the protrusions 43a, 43b, 43c, 43d can extend externally from a respective recess 116 in the exterior surface 106 of the retention clip 42 to a location spaced externally from the exterior surface 106. A first pair of the protrusions, such as the first and second protrusions 43a, 43b, can be disposed on the first clip arm 92a and a second pair of the protrusions, such as the third and fourth protrusions 43c, 43d, can be disposed on the second clip arm 92b. Each pair can include a leading protrusion, such as the first and third protrusions 43a, 43c. Each pair can also include a trailing protrusion, such as the second and fourth protrusions 43b, 43d, that are spaced from their associated leading protrusion 43a, 43c along the longitudinal direction X. The exterior surface 106 of the retention clip 42, such as on each clip arm 92a, 92b, can define a pivot or bearing portion 118 located between the respective leading protrusion 43a, 43c and the respective trailing protrusion 43b, 43d with respect to the longitudinal direction X. Each leading protrusion 43a, 43c can be coplanar with its respective trailing protrusion 43b, 43c. Stated differently, a single plane extending along the longitudinal and lateral directions X, Y can intersect the first and second protrusions 43a, 43b, such as at the apices thereof, while a single plane extending along the longitudinal and lateral directions X, Y can intersect the third and fourth protrusions 43c, 43d, such as at the apices thereof. Moreover, the leading and trailing protrusions of each pair are preferably spaced from one another such that the leading protrusion 43a, 43c of each pair is configured to reside within only one of the dimples 72 of the first set S1 of dimples of the respective array 70 while the trailing protrusion 43b, 43d of each pair is configured to reside within only one of the dimples 72 of the second set S2 of dimples of the respective array 70, as described in more detail below.

The leading protrusion 43a of the first clip arm 92a can define a first protrusion axis 45a that extends through an apex of the protrusion 43a. The trailing protrusion 43b of the first clip arm 92a can define a second protrusion axis 45b hat extends through an apex of the protrusion 43b. The leading protrusion 43c of the second clip arm 92b can define a third protrusion axis 45c that extends through an apex of the protrusion 43c. The trailing protrusion 43d of the second clip arm 92b can define a fourth protrusion axis 45d that extends through an apex of the protrusion 43d. Each protrusion 43a-d can extend externally from the exterior surface 106 along its respective protrusion axis 45a-d. The first, second, third, and fourth protrusion axes 45a-d can extend along a single common plane, which preferably is the primary reference plane P1. The first and second protrusion axes 45a, 45b can define a first angle A1 therebetween, and the third and fourth protrusion axes 45c, 45d can define a second angle A2 therebetween. The first and second angles A1, A2 can each be in a range from about 0.5 degrees to about 170 degrees, more particularly in a range from about 45 degrees to about 90 degrees, and preferably in a range from about 50 degrees to about 70 degrees. The first and second angles A1, A2 can be substantially equivalent to each other. The first and fourth protrusion axes 45a, 45d can be substantially coincident with one another when the retention clip 42 is in the unbiased configuration E1. Additionally, the second and third protrusion axes 45b, 45c can be substantially coincident with one another when the retention clip 42 is in the unbiased configuration E1. Alternatively, the first and fourth protrusion axes 45a, 45d can be offset from one another and the second and third protrusion axes 45b, 45c can be offset from one another when the retention clip 42 is in the unbiased configuration E1.

Referring now to FIGS. 5A through 5C, when a pair of links 16, such as the first link 16a and the second link 16b, are interconnected (i.e., the insertion member 26 of the first link 16a is received within the receptacle member 28 of the second link 16b) in a neutral (un-angulated) position: the longitudinal axes 21 of the first and second links 16a, 16b are preferably coincident; the lateral receptacle axes 55 and the lateral clip axes 111 of the first and second links 16a, 16b are preferably all parallel with each other; and the central hole axes 35, central receptacle axes 53, and central clip axes 109 are preferably each parallel with each other. It is to be appreciated that in other embodiments the longitudinal axis 21 of the first link 16a can extend along a direction that is angularly offset with respect to the longitudinal axis 21 of the second link 16b when the first and second links 16a, 16b are in a neutral position.

As shown in FIG. 5D, in the neutral position, the at least one protrusion 43 can reside in a respective one of the dimples 72 of the primary row RP of dimples. Particularly, with reference to the illustrated embodiment, in the neutral position, the leading protrusion 43a of the first clip arm 92a resides within the dimple 72 of the first array 70a, first set S1, primary row RP, and intermediate column C2, while the trailing protrusion 43b of the first clip arm 92a resides within the dimple 72 of the first array 70a, second set S2, primary row RP, and intermediate column C2. Moreover, in the neutral position, on the second clip arm 92b, the leading protrusion 43c resides within the dimple 72 of the second array 70b, first set S1, primary row RP, and intermediate column C2, while the trailing protrusion 43c resides with the dimple 72 of the second array 70b, second set S2, primary row RP, and intermediate column C2.

Referring now to FIG. 6A, the locking members 10, which are each insertable within one of the locking holes 8, each includes a shaft 120 that can define shaft threads 121 for threadedly purchasing with the underlying anatomical structure, and a head 122 that is coupled to the shaft 120. The locking member 10 includes an exterior surface 124 that defines the shaft threads 121, as well as external threads 126 on the head 122 that are configured to engage the internal threads 36 within the fixation hole 8 and apply the locking force to the clip arms 92a, 92b as the locking member 10 is driven through the fixation hole 8 and into the underlying anatomical structure. The threads 126 of the head 122 can define a thread profile 128 that tapers inwardly toward a central axis 129 of the locking member 10. For example, the thread profile 128 can be conical or at least frusto-conical, although other tapered profile geometries are within the scope of the present disclosure.

It is to be appreciated that, in other embodiments, at least a portion of, and up to an entirety of, the interior surface 34 within the locking hole 8 can be smooth. In such embodiments, the head of the locking member 10 can be configured as a compression screw whereby the head is unthreaded, and can abut the smooth interior surface 34 and the innermost surfaces of each projection of the clip arms 92a, 92b, thereby imparting the locking force to the clip arms 92a, 92b in the external direction as the locking member 10 is driven through the fixation hole 8 and into the underlying anatomical structure. In further embodiments, a first portion of the interior surface 34 can be smooth and devoid of threads, and a second portion of the interior surface 34 can be threaded.

Figure 6B:
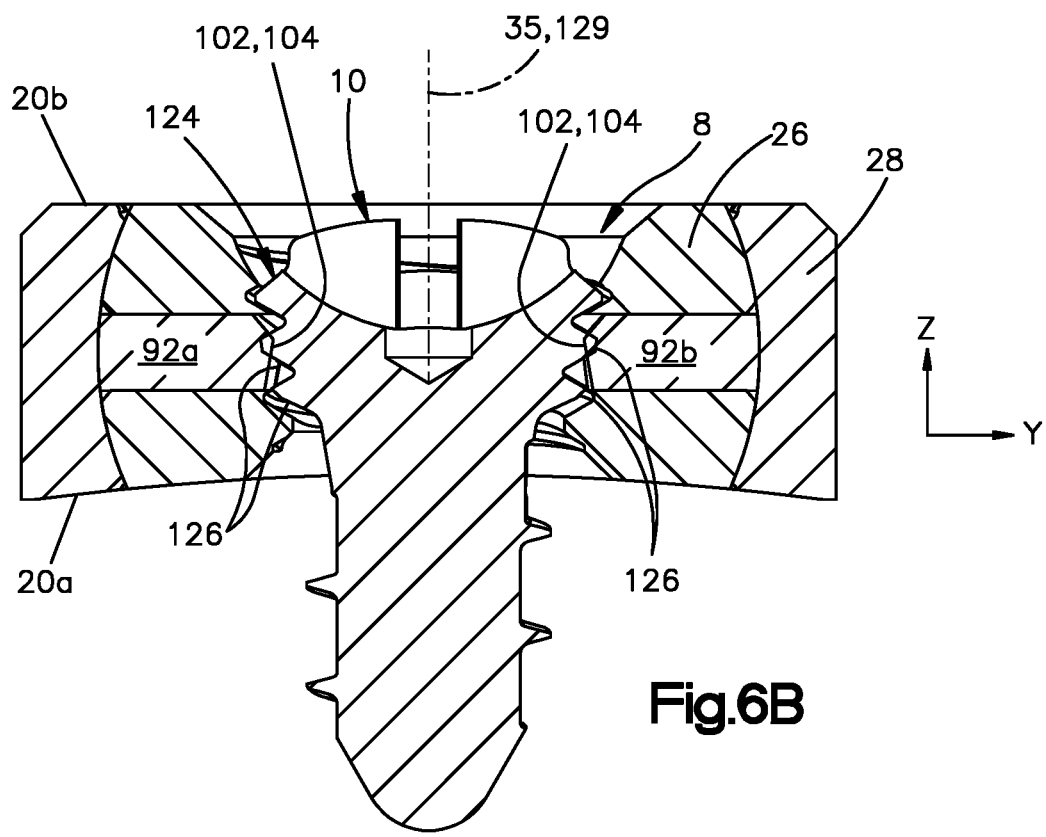
FIG. 6B is a sectional elevation view showing the locking member of FIG. 6A inserted within the linkage illustrated in FIG. 5C.
Figure 6C:
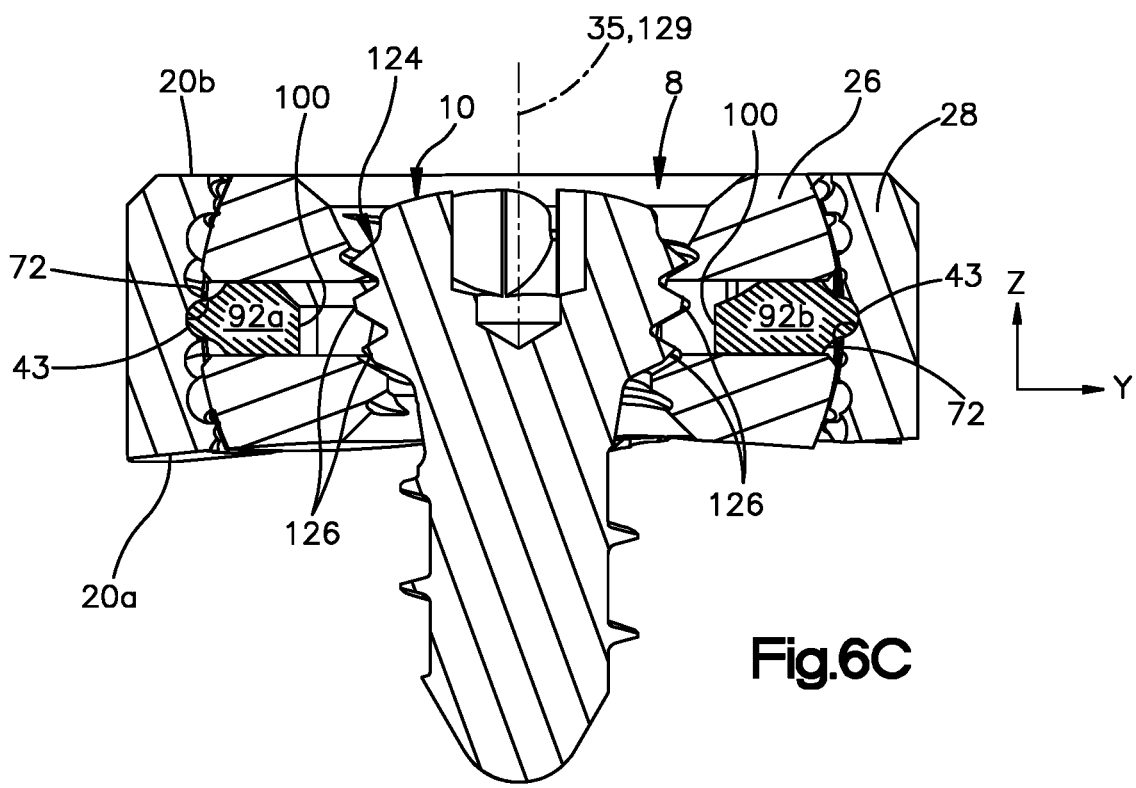
FIG. 6C is another sectional elevation view showing the locking member of FIG. 6A inserted within the linkage, taken along axis 45A shown in FIG. 4D.

Referring now to FIGS. 6B and 6C, two different section views of a joint of the linkage 6 are shown, with the insertion member 26 of the first link 16a locked within the receptacle member 28 of the second link 16b via locking engagement between the locking member 10 and the retention clip 42. In particular, at least when the locking member 10 is fully seated within the locking hole 8, the exterior surface 124 is configured to engage the first and second projections 102a, 102b so as to exert the locking force against the projections 102a, 102b, particularly against the innermost surfaces 104 thereof. At such engagement, the presence of the locking member 10 mechanically interferes with the clip arms 92a, 92b, which prevents the clip arms 92a, 92b from flexing toward one another, at least to a sufficient distance that would allow the at least one protrusion 43 to move out of the respective dimple 72. In this manner, the locking force locks the at least one protrusion 43 in the respective dimple 72, thereby locking, affixing, or otherwise maintaining the first and second links 16a, 16b at their relative position with respect to each other. It is to be appreciated that once the at least one protrusion 43 is prevented from moving out of the respective dimple 72 by the locking force, the retention clip 42 can be said to be in a locked configuration, which can coincide, at least substantially, with the unbiased configuration E1 or the intermediate configuration. It is also to be appreciated that, as used herein, the biased configuration E2 refers to a configuration of the retention clip 42 whereby the at least one protrusion 43 can move out of a respective dimple 72 in which it resides when the retention clip 42 is in the unbiased position. The tapered thread profile 128 of the head 122 provides that, as the head 122 of the locking member 10 advances within the fixation hole 8 toward the first surface 20a, the threads 126 of the head 122 progressively impinge against the innermost surfaces 104 of the projections 102a, 102b, thereby increasing the locking force.

Angulation of at least one of the first and second links 16a, 16b with respect to the other of the first and second links 16a, 16b according to various modes of angulation will now be described with reference to FIGS. 7A through 9D. In particular, in-plane angulation of the first link 16a with respect to the second link 16b about a transverse axis will be described with reference to FIGS. 7A through 7D. Out-of-plane angulation of the first link 16a with respect to the second link 16b about a lateral axis will be described with reference to FIGS. 8A through 8C. Out-of-plane, torsional angulation of the first link 16a with respect to the second link 16b about a longitudinal axis will be described with reference to FIGS. 9A through 9D.

Referring now to FIG. 7A through 7D, the links 16a, 16b can be configured to receive a force that causes the respective exterior surfaces 38, 106 of the insertion member 26 and its associated retention clip 42 of the first link 16a to ride along the interior surface 48 of the receptacle member 38 of the second link 16b such that each of the adjacent first and second links 16a, 16b can angulate in-plane along the primary reference plane about a transverse axis, such as the central hole axis 35 of the first link 16a, and thus also about the central receptacle axis 53 of the second link 16b. During such in-plane angulation, the first link 16a is configured to angulate about its central hole axis 35 until the neck 30 of the first link 16a abuts a respective one of the arms 56a, 56b that defines the channel 58. The first link 16a can angulate in-plane with respect to the second link 16b at an in-plane angle A3 measured between the longitudinal axes 21 of the first and second links 16a, 16b. Thus, the total in-plane angulation range between the first and second links 16a, 16b can be characterized as two times A3 (i.e., A3×2). The in plane angle A3 can be in a range of about 0 degrees to about 90 degrees, and more particularly in a range of about 10 degrees to about 40 degrees, and yet more particularly in a range of about 10 degrees and about 20 degrees. It is to be appreciated that the maximum in plane angle A3 can be limited by the geometry of the at least one dimple array 70 and/or by interference between the neck 30 and the trailing ends 62 of the arms 56a, 56b of the receptacle member 28.

Figure 7A:
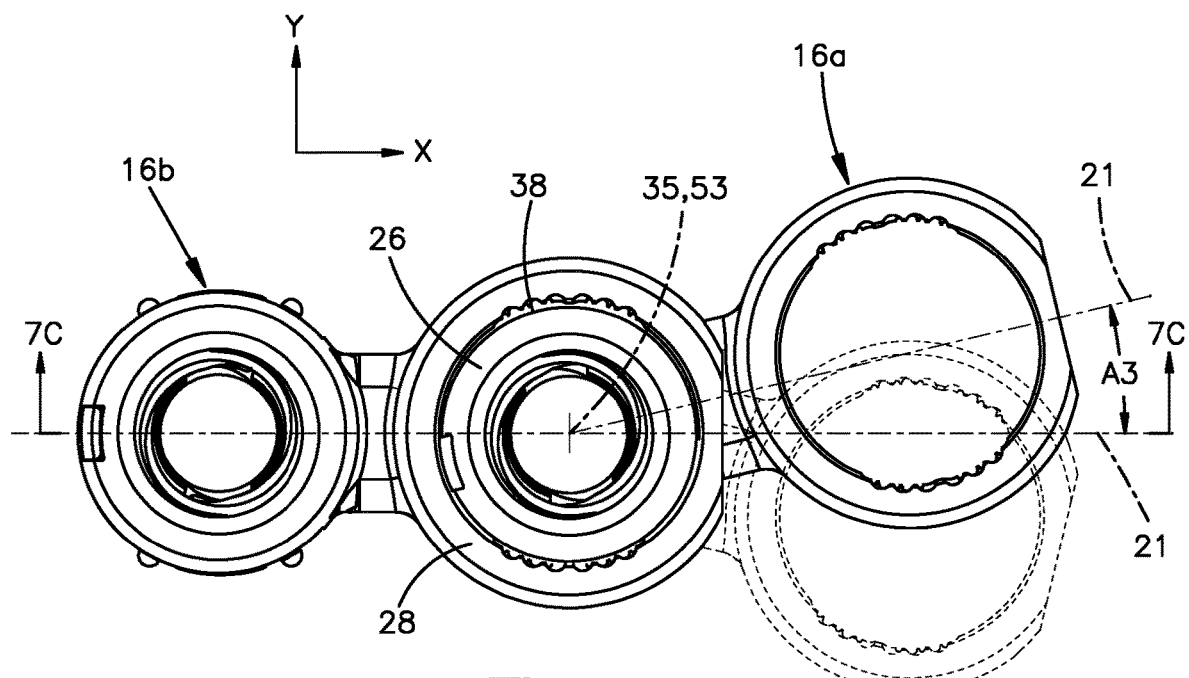
FIG. 7A is a top plan view of the linkage illustrated in FIG. 5A, shown in an angulated position about a transverse axis.
Figure 7B:
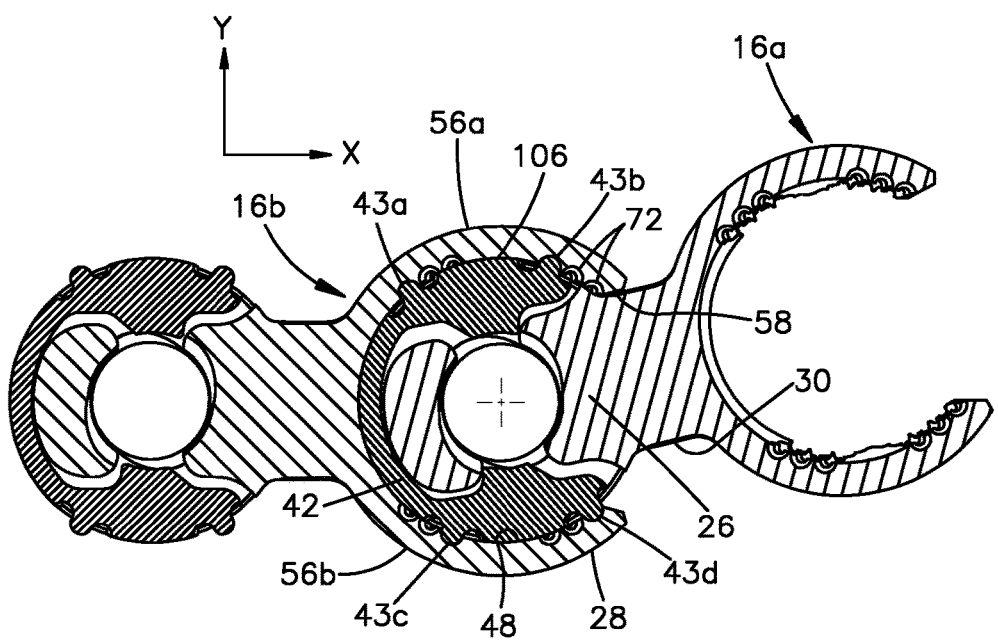
FIG. 7B is a sectional top plan view of the linkage illustrated in FIG. 7A, taken along a plane extending along a longitudinal direction and a lateral direction.
Figure 7C:
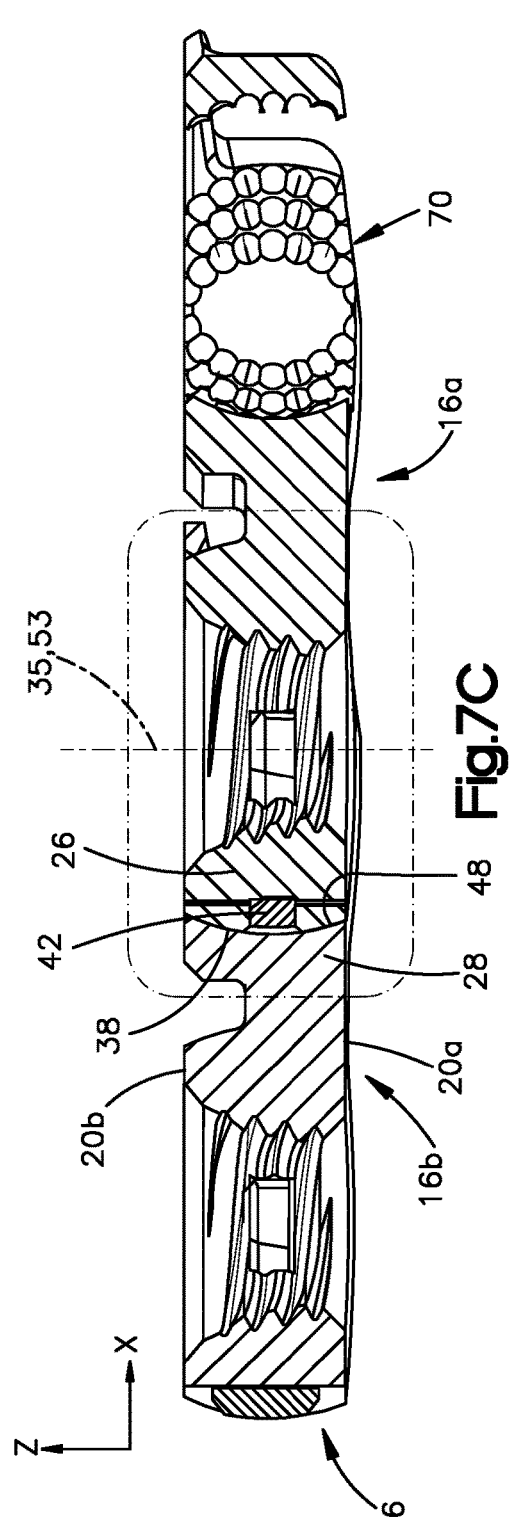
FIG. 7C is a sectional side elevation view taken along section line 7C-7C of FIG. 7A.
Figure 7D:
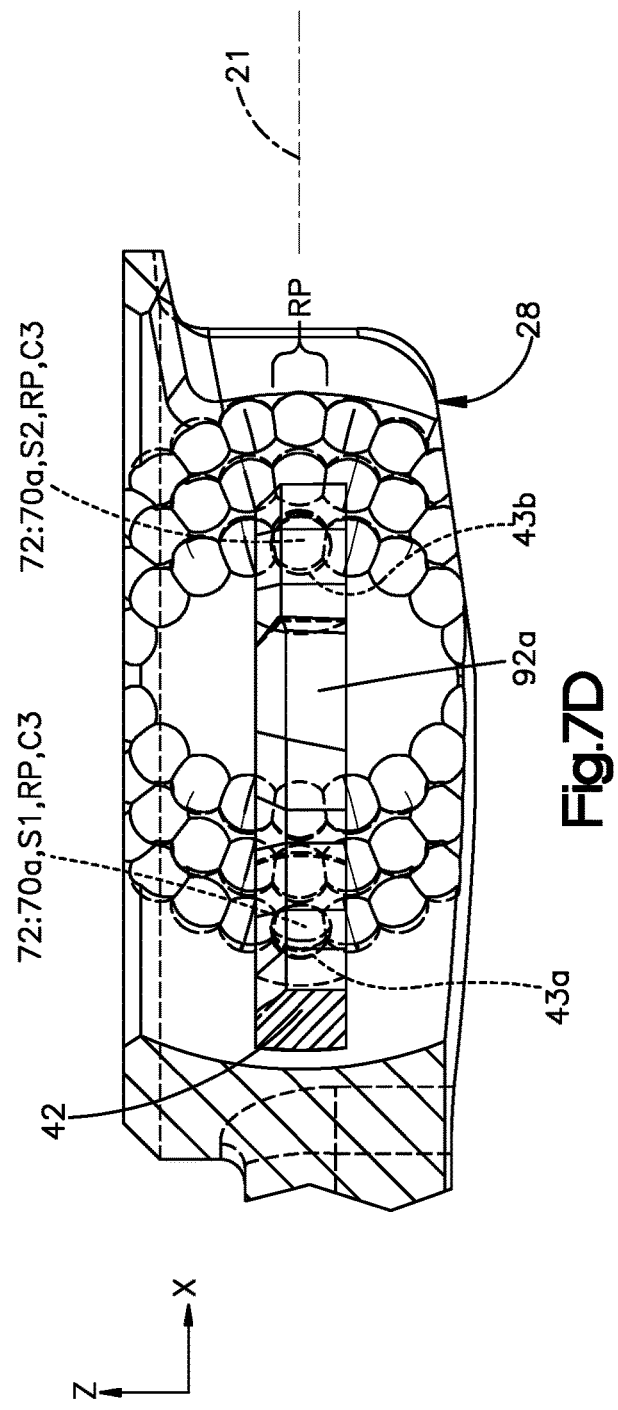
FIG. 7D is a magnified view of a joint of the linkage illustrated in FIG. 7C, with the first link removed for illustrated purposes.

As the first link 16a angulates in-plane about its central hole axis 35, the at least one protrusion 43, such as each of protrusions 43a-d, can snap in and out of dimples 72 of the primary row RP of dimples. As shown in FIGS. 7B and 7D with reference to the illustrated example embodiment, at a maximum in-plane angulation, the leading protrusion 43a on the first clip arm 92a can reside within the dimple 72 of the first array 70a, first set S1, primary row RP, and outermost column C3, while the trailing protrusion 43b on the same clip arm 92a can reside within the dimple 72 of the first array 70a, second set S2, primary row RP, and innermost column C1. On the second clip arm 92b, the leading protrusion 43c can reside within the dimple 72 of the second array 70b, first set S1, primary row RP, and innermost column C1, while the trailing protrusion 43d can reside within the dimple 72 of the second array 70b, second set S2, primary row RP, and outermost column C3. It is to be appreciated that the foregoing protrusion 43 and dimple 72 engagements at a maximum in-plane angulation are provided as a non-limiting example, and other protrusion-to-dimple engagements at maximum in-plane angulation are within the scope of the present disclosure.

Referring to FIGS. 8A through 8D, the first and second links 16a, 16b can be configured to receive a force that causes the respective exterior surfaces 38, 106 of the first link 16a and retention clip 42 to ride along the interior surface 48 of the second link 16b such that each of the adjacent first and second links 16a, 16b can angulate out-of-plane with respect to the other of the first and second links 16a, 16b about a lateral axis, such as the lateral receptacle axis 55, and thus along a plane that is defined by the transverse direction Z and the longitudinal direction X, such as the secondary reference plane. Such angulation can be referred to as "transverse out-out-plane angulation" or simply "transverse angulation". As the first and second links 16a, 16b angulate out-of-plane with respect to each other about the lateral receptacle axis 55 of the second link 16b, the at least one protrusion 43, such as each of protrusions 43a-d, can snap in and out of dimples 72 of a single respective column C of dimples.

Figures 8A, 8B:
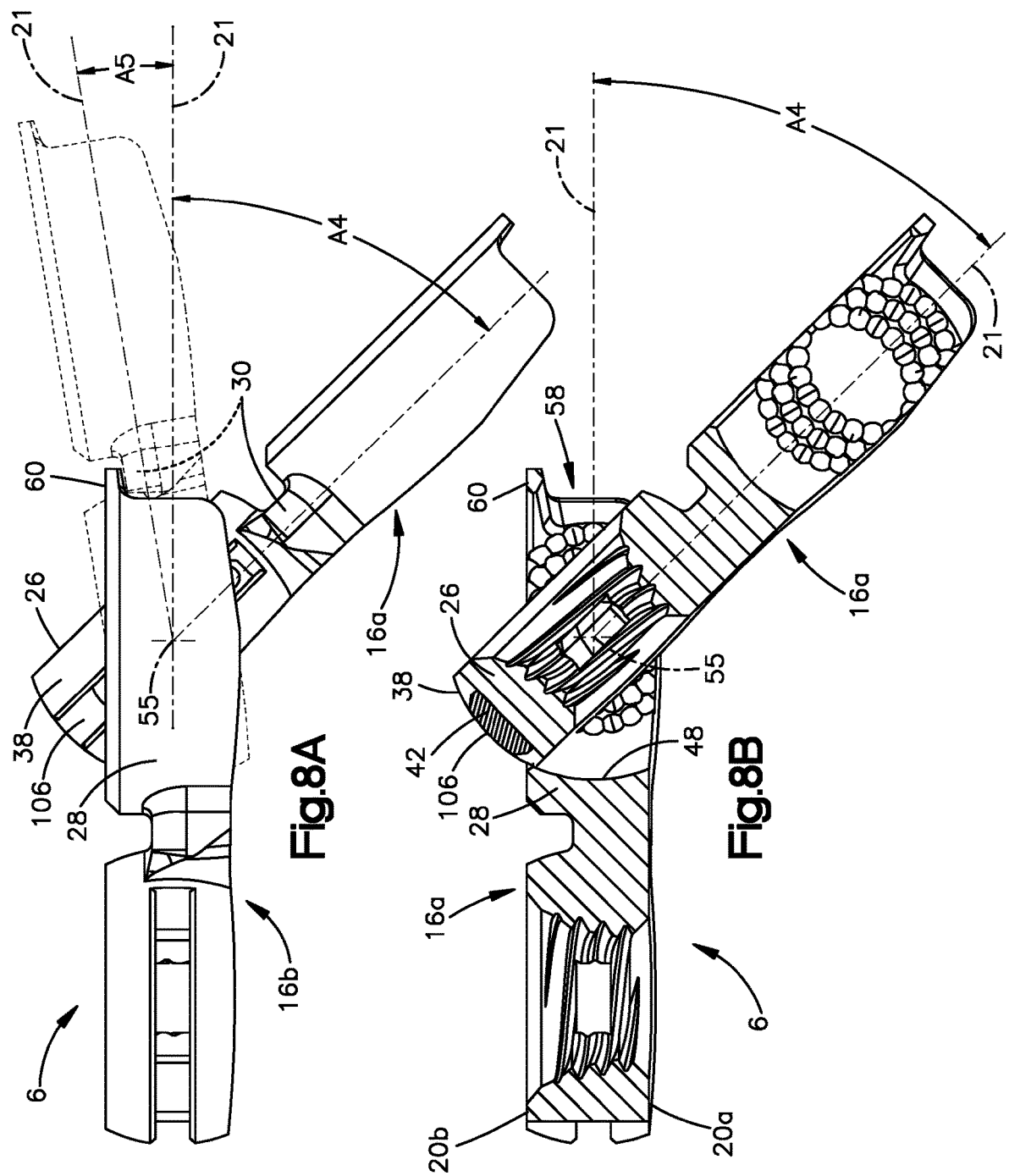
FIG. 8A is a side elevation view of the linkage illustrated in FIG. 5A, shown in an angulated position about a lateral axis.
FIG. 8B is a sectional side elevation view of the linkage illustrated in FIG. 5A, taken along a plane extending along the longitudinal direction and a transverse direction.

Because the channel 58 is open to the first side 18a of the receptacle member 28, the first link 16a can angulate with respect to the second link 16b about the lateral receptacle axis 55 of the second link 16b along a direction from the second side 18b to the first side 18a (i.e., toward the underlying anatomical structure) without either of the links 16a, 16b interfering with the other of the links 16a, 16b. Moreover, as shown in FIGS. 8A and 8B, the links 16a, 16b can be configured so as to angulate with respect to each other about the lateral receptacle axis 55 of the second link 16b in a direction away from the bridge 60 a sufficient amount so as to bring the neck 16 of the first link 16a out of alignment with the arms 56a, 56b of the second link 16b with respect to the lateral direction Y.

Conversely, because the receptacle member 28 can include the bridge 60 that is connected between the arms 56a, 56b, the bridge 60 can be configured to contact the neck 30 of the first link 16a as the first link 16a angulates with respect to the second link 16b about the lateral receptacle axis 55 along a direction from the first side 18a toward the second side 18b. Thus, the receptacle member 28, and in particular the bridge 60, can define a stop that limits angulation of the first link 16a with respect to the second link 16b about the lateral receptacle axis 55 in a direction toward the bridge 60. In embodiments where the curvature of the outer surface the underlying anatomical structure is more likely to be convex to a greater degree than it is concave, it may be desirable to allow for more angulation about the lateral receptacle axis 55 in the direction from the second side 18b toward the first side 18a than angulation about the lateral transverse axis in the direction from the second side 18b toward the first side 18a, such that the first side 18a of the linkage 6 conforms to the surface of the underlying anatomical structure. Thus, in such embodiments, the bridge 60 is preferably located proximate the second side 18b and remote from the first side 18a, as in the illustrated embodiment.

The first link 16a can angulate transversely out-of-plane toward the underlying anatomy relative to the second link 16b at an angle A4 measured between the longitudinal axes 21 of the first and second links 16a, 16b, which angle A4 can be in a range of about 0 degrees to about 90 degrees, and more particularly in a range of about 30 degree to about 80 degrees, and yet more particularly in a range of about 55 degrees to about 64 degrees. The first link 16a can also angulate transversely out-of-plane away from the underlying anatomy relative to the second link 16b at an angle A5 measured between the longitudinal axes 21 of the first and second links 16a, 16b, which angle A5 can be in a range of about 0 degrees to about 45 degrees, and more particularly in a range of about 5 degrees to about 30 degrees, and yet more particularly in a range of about 10 degrees to about 20 degrees. It is to be appreciated that the maximum of angles A4 and A5 can be limited by the geometry of one or both of the first and second links 16a, 16b, such as the geometry of the at least one dimple array 70 and/or by interference between the bridge 60 of the second link 16b and the neck 30 of the first link 16a, for example. The total transverse out-of-plane angulation range between the first and second links 16a, 16b can be characterized as the sum of A4 and A5. As mentioned above, the bridge 60 can alternatively be located proximate the first side 18a and remote from the second side 18b. In such embodiments, angle A4 can be in a range of about 0 degrees and about 45 degrees, while angle A5 can be in a range of about 0 degrees to about 90 degrees.

With reference to FIG. 8C, in the illustrated example embodiment, and at a maximum out-of-plane angulation about the lateral receptacle axis 55 of the second link 16b in a direction from the second side 18b toward the first side 18a, the leading protrusion 43a of the first clip arm 92a can reside within the dimple 72 of the first array 70a, first set S1, third upper row RU3, and intermediate column C2, while the trailing protrusion 43b of the first clip arm 92b can reside within the dimple 72 of the first array 70a, second set S2, third lower row RL3, and intermediate column C2. Although not visible in the view of FIG. 8C, it is to be appreciated that, in the present example embodiment, the leading protrusion 43c of the second clip arm 92b can reside within the dimple 72 of the second array 70b, first set S1, third upper row RU3, and intermediate column C2, while the trailing protrusion 43d of the second clip arm 92b can reside within the dimple 72 of the second array 70b, second set S2, third lower row RL3, and intermediate column C2. It is to be appreciated that the foregoing protrusion 43 and dimple 72 engagements at a maximum out-of-plane angulation are provided as a non-limiting example, and other protrusion-to-dimple engagements at maximum out-of-plane angulation are within the scope of the present disclosure.

Figure 9A:
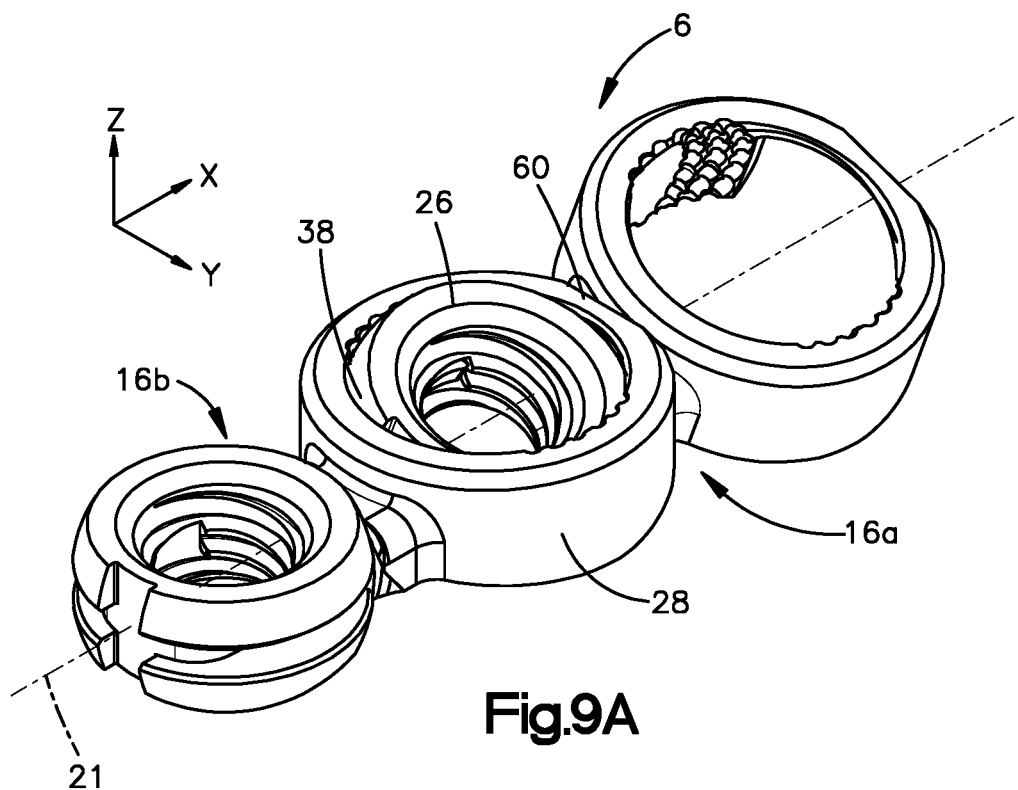
FIG. 9A is a perspective view of the linkage illustrated in FIG. 5A, shown in an angulated position about a longitudinal axis.
Figure 9B:
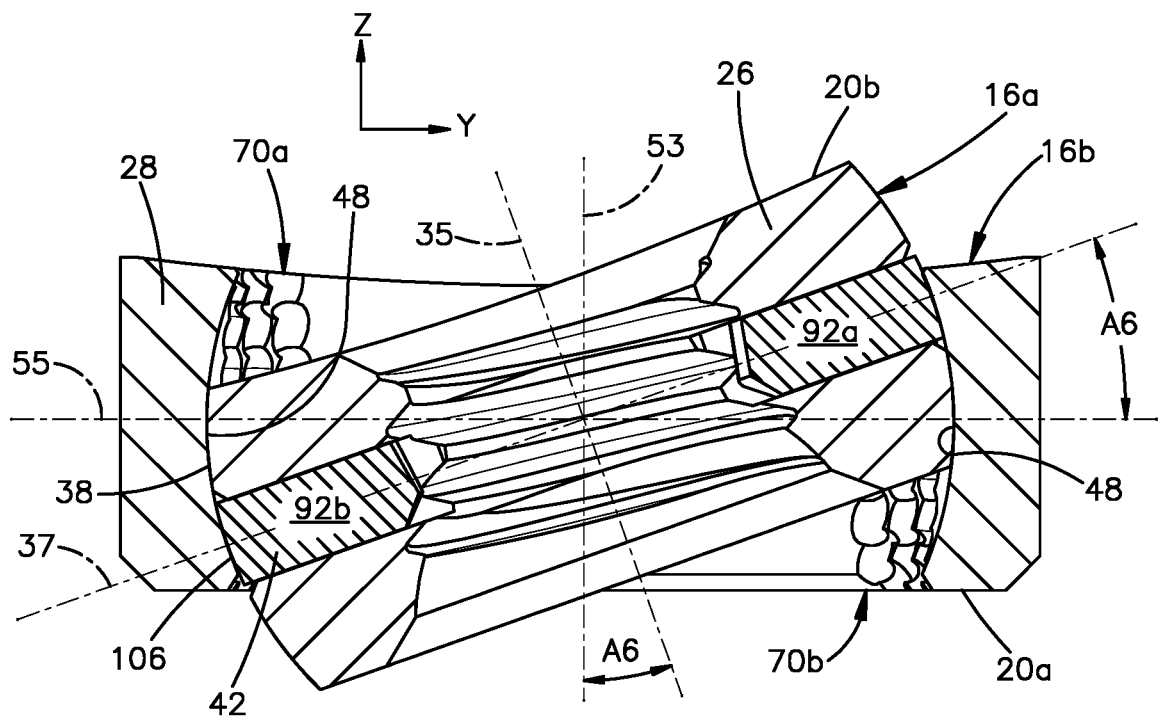
FIG. 9B is a sectional end elevation view of the linkage taken along a section line intersecting a geometric center of a joint of the linkage illustrated FIG. 9A.

Referring now to FIGS. 9A through 9D, the links 16a, 16b can be configured to receive a force that causes the respective exterior surfaces 38, 106 of the first link 16a and retention clip 42 to ride along the interior surface 48 of the second link 16b such that each of the adjacent first and second links 16a, 16b can angulate torsionally out-of-plane with respect to the other of the first and second links 16a, 16b about the longitudinal axis 21 of at least one of the links 16a, 16b. The links 16a, 16b are configured to angulate torsionally about the longitudinal axis 21 until the neck 30 of the first link 16a abuts the bridge 60 of the second link 16b, which can define a stop surface that abuts the first link 16a and limits angulation of the first and second links 16a, 16b with respect to each other about the longitudinal axis 21. As shown in FIG. 9B, the first link 16a can angulate torsionally with respect to the second link 16b at a torsional angle A6, which can be measured, for example, between the central hole axis 35 of the first link 16a and the central receptacle axis 53 of the second link 16b. The torsional angle A6 can also be measured between the lateral hole axis 37 of the first link 16a and the lateral receptacle axis 55 of the second link 16b. The total torsional angulation range between the first and second links 16a, 16b can be characterized as two times A6 (i.e., A6×2). The torsional angle A6 can be in a range of about 0 degrees to about 90 degrees, and more particularly in a range of about 15 degrees to about 60 degrees, and yet more particularly in a range of about 20 degrees to about 30 degrees. It is to be appreciated that the maximum torsional angle A6 can be limited by the geometry of the at least one dimple array 70 and/or by interference between the bridge 60 and the neck 30.

As the first and second links 16a, 16b angulate torsionally out-of-plane with respect to each other about the longitudinal axis 21, the at least one protrusion 43, such as each of protrusions 43a-d, can snap in and out of dimples 72 of one or more columns C and at least two or more rows R of dimples 72. With reference to FIG. 9D, in the illustrated example embodiment, and at a maximum torsional angulation about the longitudinal axis 21, the leading protrusion 43a of the first clip arm 92a resides within the dimple 72 of the first array 70a, first set S1, third upper row RU3, and outermost column C3, while the trailing protrusion 43b of the first clip arm 92a resides within the dimple 72 of the first array 70a, second set S2, third upper row RU3, and outermost column C3. On the second clip arm 92b, the leading protrusion 43c resides within the dimple 72 of the second array 70b, first set S1, third lower row RL3, and outermost column C3, while the trailing protrusion 43d resides within the dimple 72 of the second array 70b, second set S2, third lower row RL3, and outermost column C3. It is to be appreciated that the foregoing protrusion 43 and dimple 72 engagements at a maximum torsional angulation are provided as a non-limiting example, and other protrusion-to-dimple engagements at maximum torsional angulation are within the scope of the present disclosure.

It is to be appreciated that the first and second links 16a, 16b are also configured to angulate with respect to each other polyaxially about two or more axes, including three axes extending respectively along the longitudinal, lateral, and transverse directions X, Y, Z, which preferably intersect one another at a common point, which can be located at the centroid of the spherical shapes that define the exterior surfaces 38, 106 and the interior surface 48, as in the illustrated embodiments. For example, the first and second links 16a, 16b are configured to angulate with respect to each other about any combination of, including all of, the longitudinal axis 21, central hole axis 35, and lateral hole axis 37 of the first link 16a as well as the longitudinal axis 21, central receptacle axis 53, and lateral receptacle axis 55 of the second link 16b. It is to be appreciated that the longitudinal, lateral, and transverse axes of angulation can intersect each other at different locations, for instance when the insertion member 26 of the first link 16a is loosely received in the receptacle 52 of the second link 16b.

As the first and second links 16a, 16b angulate with respect to each other about one or more of longitudinal, lateral, and transverse axes, the at least one protrusion 43 can snap in and out of various dimples 72 of the respective array 70 as the protrusion 43 rides along the retention structure of the interior surface 48. Each snap can provide the physician with indicia of the angulation between the first and second links 16a, 16b about one, two, or three of the longitudinal, lateral, and transverse axes. Such indicia can include audible feedback, such as a snapping or clicking sound perceivable by the physician as each protrusion 43 snaps externally into a respective dimple 72. Such indicia can also include tactile feedback perceivable by the physician as each protrusion 43 snaps into a respective dimple 72. Thus, in one example method of shaping a linkage 6, a physician can interconnecting the first and second links 16a, 16b so that they are in the neutral position, from which the physician can then angulate the first and second links 16a, 16b with respect to each other about one axis and observe the number of snaps to gain at least an estimation of the degree of angulation about the axis. Subsequently, angulation between the first and second links 16a, 16b can be performed about a second axis, and the physician can observe the number of snaps to gain at least an estimation of the degree of angulation about the second axis in like manner. The process can be repeated for angulation about a third axis. Thus, each dimple of a respective array 70 can be characterized as an angulation "setting," which can be observed audibly and/or tactilely via one or both of the foregoing indicia. The foregoing indicia provide distinct advantages over prior art linkages, at least as a result of being observable without a direct line of sight to the linkage, and even without any view of the linkage.

It is to be appreciated that the foregoing maximum angulation angles A3-A6 can be adjusted by modifying the at least one dimple array 70. For example, it can be said that the first and second dimple arrays 70a, 70b of the illustrated embodiment are configured to favor transverse out-out-plane angulation relative to in-plane angulation and torsional angulation. However, in other embodiments, the at least one dimple array 70 can be modified to increase in-plane angulation (such as by including additional intermediate columns C2 of dimples 72) and/or to increase torsional angulation (such as by including additional rows R of dimples 72). Modifications to the neck 30, bridge 60, and/or the trailing ends 62 of the arms 56a, 56b can also facilitate adjustments to the maximum angulation angles A3-A6. Moreover, the size of the dimples 72 and the corresponding size of the at least one protrusion 43 can be adjusted so as to provide more of fewer dimples 72 on the links 16 as desired. For example, each set S can have two, three, four, five, six, seven, eight, nine, ten, eleven, twelve, or more than twelve intermediate columns C2 of dimples 72. Similarly, each set S can have two, three, four, five, six, seven, eight, nine, ten, eleven, twelve, thirteen, fourteen, fifteen, sixteen, seventeen, eighteen, nineteen, twenty, or more than twenty rows R of dimples 72.

As mentioned above, the retention clip 42 can be alternatively configured so that the at least one protrusion 43 is spaced radially inward from at least one dimple adjacent 72 when the retention clip 42 is in the unbiased configuration, and the at least one protrusion is fully seated within at least one adjacent dimple 72 when the retention clip 42 is in the biased configuration. In such embodiments, instead of the snapping or clicking engagement between the at least one protrusion and the dimples 72 as the insertion member 28 angulates within the receptacle 52, the insertion member 28 can angulate within the receptacle without contact between the at least one protrusion 42 and the interior surface 48 (including the dimples 72) of the receptacle member 28, and then insertion of the locking member 10 can push the clip arms 92a, 92b radially outward until the at least one protrusion 43 is fully seated within the respective at least one dimple 72.

In other embodiments, the retention clip 42 can employ female retention features, such as dimples 70, and the retention structure on the interior surface 48 of the receptacle member 28 can employ male retention features, such as protrusions 43. In such embodiments, the retention structure on the interior surface 48 can define one or more arrays of protrusions that are arranged generally similar to the dimple arrays 70 described above, while the retention clip 42 can include at least one and preferably a plurality of dimples having a complimentary geometry to that of the protrusions on the interior surface 48. The angulation and locking functions the linkages 6 of such an embodiment can operate similarly to the embodiments described above with reference to FIGS. 1-9D.

In other embodiments, the receptacle member 28 of at least one of the links 16 can be "open" at its trailing end by being devoid of the bridge 60, as more fully described in U.S. Patent Publication No. 2015/0018829 A1, published Jan. 15, 2018, in the name of Woodburn et al. (the "Woodburn Reference"), the entire disclosure of which is hereby incorporated by reference into this patent application. Thus, in such embodiments, at least a portion up to an entirety of the channel 58 can extend from the first surface 20a to the second surface 20b between the arms 56a, 56b, which can increase angulation out-of-plane angulation between the first and second links 16a, 16b about a transverse axis and in a direction from the first surface 20a to the second surface 20b of the second link 16b.

In yet other embodiments, the receptacle member 28 of at least one of the links 16 can be configured such that the channel 58 is offset from the longitudinal direction X, as more fully described in the Woodburn Reference with reference to FIGS. 8A through 8B thereof. Thus, in such embodiments, the longitudinal axis 21 of the link 16 may be located closer to one trailing end 62 than the other with respect to the lateral direction Y. In such embodiment, the longitudinal axis 21 of the link 16 may optionally extend through one of the arms 56a, 56b but not between the trailing ends 62 of the arms 56a, 56b.

In yet further embodiments, at least one of the links 16 can be pre-bent, that is to say that such a link 16 can be configured such that the neck 30 is pre-bent or curved, such as in the transverse direction Z, for example, as more fully described in the Woodburn Reference with reference to FIGS. 9A through 9B thereof. Thus, in such embodiments, the central hole axis 35 and the central receptacle axis 53 of the link 16 can each extend along the secondary reference plane and can be offset from one another at an angle. Pre-bent links 16 can be configured to accommodate specific patient anatomies that involve compound angles at the boney surface. It is to be appreciated that pre-bent links 16 can include multiple bends, such as at the neck 30. In even further embodiments, one or more portions of at least one of the links 16 can have a region, such as at the neck 30, for example, that is plastically deformable so as to be bent as needed to accommodate the geometry of the underlying anatomy.

In additional embodiments, the bone fixation linkage 6 can include at least one cap that is configured to interconnect with at least one of the links 16, as more fully described in the Woodburn Reference with reference to FIGS. 10A through 11B thereof. In such embodiments, for example, the receptacle member 28 of the trailing end-most link 16 can have a cap configured similarly to an insertion member 26 (and associated retention clip 42) described above received therein. In such embodiments, the relative positions between the receptacle member 28 and the cap can be affixed via a locking member 10 inserted within the fixation hole 8 of the cap, similar to the manner described above with respect to first and second links 16a, 16b. Additionally, in such embodiments, the insertion member 26 (and its retention clip 42) of the leading-most link 16 in the linkage 6 can be inserted within a cap that is configured similarly to a receptacle member 28 described herein, and the relative positions between the insertion member 26 and the cap can be affixed via a locking member 10 inserted within the fixation hole 8 of the insertion member 26, similar to the manner described above with respect to first and second links 16a, 16b.

In yet additional embodiments, one or more of the links 16 of the bone fixation linkage 6 can be configured as a plate having a plate body and at least one attachment member 24a, 24b monolithic with the plate body, which attachment member can be configured as a receptacle member 28 or an insertion member 26 of the respective types described above. Such a link 16 can be configured as more fully described in the Woodburn Reference with reference to FIGS. 15A through 15D thereof.

In further embodiments, one or more of the links 16 can include two or more insertion members 26 without any receptacle members 28, or two or more receptacle members 28 without any insertion members 26, as more fully described in the Woodburn Reference with reference to FIGS. 16C and 16D thereof.

In yet further embodiments, one or more of the links 16 can include more than two attachment members 24a, 24b, as more fully described in the Woodburn Reference with reference to FIGS. 16A and 16B thereof. For example, in such embodiments, one or more of the links 16 can include, at least one insertion member 26 and two or more receptacle members 28, at least one receptacle member 28 and two or more insertion members 26, and/or more than two insertion members 26 and more than two receptacle members 28. It is to be appreciated that the links 16 can include any number of insertion members 26 and any number of receptacle members 28 as needed.

Although the disclosure has been described in detail, it should be understood that various changes, substitutions, and alterations can be made herein without departing from the spirit and scope of the invention as defined by the appended claims. It is also to be appreciated that one or more elements, features, components, and/or structures of one of the embodiments can be employed in other embodiments. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A linkage for affixation to bone, comprising:
    a first link and a second link each comprising:
        a receptacle member having an interior surface that defines a receptacle, the interior surface defining a plurality of retention features;
        an insertion member extending from the receptacle member, the insertion member defining an exterior surface at least partially surrounding a hole, the exterior surface defining a recess, the insertion member defining at least one opening extending from the recess to the hole, wherein the exterior surface of the first link is configured to reside within the receptacle of the second link; and
        a retention member configured to reside within the recess, the retention member defining:
            at least one retention feature configured to engage the plurality of retention features of the interior surface;
            at least one projection configured to extend internally through the at least one opening and into the hole,
        wherein the retention member is flexible between a first configuration and a second configuration such that, in the first configuration, the at least one retention feature is engaged with a respective one of the plurality of retention features, and in the second configuration, the at least one retention feature is spaced from the respective one of the plurality of retention features.

2. The linkage of claim 1, further comprising a locking member insertable within the hole, the locking member having an exterior surface configured to engage the at least one projection when the locking member is seated within the hole, thereby exerting a locking force against the at least one projection that prevents the at least one retention feature from disengaging the respective one of the plurality of retention features in a manner affixing a relative position between the first and second links.

3. The linkage of claim 2, wherein the at least one retention feature is at least one protrusion, the plurality of retention features are a plurality of dimples, such that, in the first configuration, the at least one protrusion extends away from a central axis of the hole at a first distance, and, in the second configuration, the at least one protrusion extends away from the central axis of the hole at a second distance that is less than the first distance.

4. The linkage of claim 2, wherein:
    within the hole of each of the first and second links, the insertion member defines internal threads;
    the locking member is a bone screw having a head, the exterior surface of the locking member comprises external threads on the head; and
    the at least one projection of the retention member defines an inner surface that is substantially smooth and is configured to receive the locking force transmitted by the external threads on the head of the bone screw.

5. The linkage of claim 1, wherein the interior surface defines a bearing surface, the plurality of retention features are arranged around the bearing surface, and the bearing surface defines a contour that is one or more of substantially smooth and substantially spherical.

6. The linkage of claim 1, wherein the plurality of retention features are arranged in rows of retention features, and each row extends along a respective plane.

7. The linkage of claim 6, wherein the plurality of retention features are further arranged in columns of retention features, the receptacle extends along a central receptacle axis, the hole extends along a central hole axis, and each column follows a path that is curved as viewed from a transverse reference plane that contains each of the central receptacle axis and the central hole axis.

8. The linkage of claim 1, wherein:
    the at least retention feature is at least one protrusion;
    the plurality of retention features are an array of dimples arranged around a bearing surface defined by the interior surface;
    the array of dimples comprises 1) a first set of rows and columns of dimples on a leading side of the bearing surface, and 2) a second set of rows and columns of dimples on a trailing side of the bearing surface; and
    the at least one protrusion comprises a leading protrusion and a trailing protrusion coplanar with one another, wherein the leading and trailing protrusions are spaced from one another such that the leading protrusion is configured to reside within only the dimples of the first set of rows and columns of dimples while the trailing protrusion is configured to reside within only the dimples of the second set of rows and columns of dimples.

9. The linkage of claim 1, wherein the exterior surface of the insertion member defines a notch, and the retention member defines a rib configured to reside in the notch so as to retain relative positions between the retention member and the insertion member.

10. The linkage of claim 1, wherein the retention member is a C-clip.

11. A link for interconnecting with one or more additional, similarly configured links so as to form a linkage for affixation to bone, comprising:
    a receptacle member having an interior surface that defines a receptacle, the interior surface defining a bearing surface and an array of retention features arranged around the bearing surface, wherein the bearing surface is smooth and defines a segment of a sphere, and the bearing surface is spatially separate from the array of retention features; and
    an insertion member extending from the receptacle member, the insertion member defining an exterior surface at least partially surrounding a hole, wherein a geometry of the exterior surface is configured to fit within a geometry of the receptacle such that the bearing surface is configured to engage a corresponding portion of the exterior surface of the insertion member, the exterior surface defining an annular recess configured to receive a retention member for engaging one or more of the arrayed retention features.

12. The link of claim 11, wherein the exterior surface of the insertion member is substantially spherical, and the interior surface of the receptacle member is substantially spherical.

13. The link of claim 11, wherein the insertion member and the receptacle member are spaced from each other along a longitudinal direction, the bearing surface is a first bearing surface and the array of retention features is a first array of retention features arranged in rows and columns around the first bearing surface, the interior surface defines a second bearing surface spaced from the first bearing surface along a lateral direction substantially perpendicular to the longitudinal direction, the interior surface defines a second array of retention features arranged in rows and columns around the second bearing surface, and each of the retention features of the first and second arrays of retention features is configured to engage at least one complimentary engagement feature of the retention member.

14. The link of claim 13, wherein the link defines a longitudinal axis oriented along the longitudinal direction, a lateral axis oriented along the lateral direction and intersecting respective centerpoints of the first and second bearing surfaces, and a reference plane that contains the longitudinal and lateral axes.

15. The link of claim 14, wherein each row extends annularly along a respective plane that is parallel with the reference plane.

16. The link of claim 14, wherein each column follows a path that is curved as viewed from a transverse reference plane that contains the longitudinal axis and is perpendicular to the reference plane.

17. The link of claim 16, wherein the path of each column is substantially semi-circular or substantially semi-elliptical when viewed in the transverse reference plane.

18. The link of claim 13, wherein the retention features of the first and second arrays each define a spherical geometry that is one of male and female, and the at least one complimentary engagement feature defines a spherical geometry that is the other of male and female and is complimentary with the spherical geometry of each retention feature of at least one of the first and second arrays.

19. The link of claim 18, wherein each of the retention features of the first and second arrays is a dimple, and the at least one complimentary engagement feature is a protrusion.

20. The link of claim 19, wherein:
the link defines a neck between the receptacle member and the insertion member;
the receptacle member includes:
   a pair of arms extending away from the insertion member; and
   a bridge interconnecting trailing ends of the pair of arms, wherein the link defines a channel that extends 1) between the pair of arms along the lateral direction, and 2) from a bone-facing surface of the receptacle member to the bridge along a transverse direction that is substantially perpendicular to the longitudinal and lateral directions,
wherein the channel is sized to receive the neck of a similarly configured link while allowing the insertion member of the similarly configured link to reside within the receptacle while also inhibiting the insertion member of the similarly configured link from withdrawing from the receptacle along the longitudinal direction.

* * * * *